United States Patent
Marchand

(10) Patent No.: US 10,952,851 B2
(45) Date of Patent: Mar. 23, 2021

(54) DELIVERY APPARATUS FOR SELF-EXPANDING MEDICAL DEVICE

(71) Applicant: Tricares (SAS), Paris (FR)

(72) Inventor: Coralie Marchand, Munich (DE)

(73) Assignee: TRICARES (SAS), Paris (FR)

( * ) Notice: Subject to any disclaimer, the term of this patent is extended or adjusted under 35 U.S.C. 154(b) by 166 days.

(21) Appl. No.: 15/745,921

(22) PCT Filed: Jul. 20, 2016

(86) PCT No.: PCT/EP2016/067336
§ 371 (c)(1),
(2) Date: Jan. 18, 2018

(87) PCT Pub. No.: WO2017/013187
PCT Pub. Date: Jan. 26, 2017

(65) Prior Publication Data
US 2018/0206990 A1 Jul. 26, 2018

Related U.S. Application Data

(60) Provisional application No. 62/194,490, filed on Jul. 20, 2015.

(30) Foreign Application Priority Data

Dec. 2, 2015 (EP) .................................... 15197658

(51) Int. Cl.
A61F 2/24 (2006.01)
A61F 2/962 (2013.01)
(Continued)

(52) U.S. Cl.
CPC .......... *A61F 2/2439* (2013.01); *A61F 2/2436* (2013.01); *A61F 2/95* (2013.01);
(Continued)

(58) Field of Classification Search
CPC ...... A61F 2002/9511; A61F 2002/9505; A61F 2002/9665; A61F 2002/9517; A61F 2/95;
(Continued)

(56) References Cited

U.S. PATENT DOCUMENTS 5,840,081 A 11/1998 Andersen et al.
5,925,076 A 7/1999 Inoue
(Continued)

FOREIGN PATENT DOCUMENTS

EP 1440673 A1 7/2004
EP 1728477 A1 12/2006
(Continued)

OTHER PUBLICATIONS

International Search Report and Written Opinion, Application No. PCT/EP2016/067336, dated Sep. 29, 2016.
(Continued)

*Primary Examiner* — Katherine M Shi
(74) *Attorney, Agent, or Firm* — The Dobrusin Law Firm, P.C.

(57) ABSTRACT

The present invention relates to a delivery apparatus for delivering a radially self-expanding medical device (2) having a proximal portion and a distal portion, said delivery apparatus comprising an elongated tubular member having a proximal end, a distal end and a lumen (122) extending along a longitudinal axis from the proximal end to the distal end; a sheath (11), said sheath (11) being coaxially disposed around the elongated tubular member (12); wherein the elongated tubular member (12) is movable relative to the sheath (11); and wherein the sheath (11) is configured for receiving the radially self-expanding medical device (2) in a radially compressed state; and a holding and retrieving mechanism configured to constrain radially the proximal portion of the radially self-expanding medical device (2)
(Continued)

such that in response to a proximal movement of the elongated tubular member (12) relative to the sheath (11), the holding and retrieving mechanism (13) constrains radially the proximal portion of the radially self-expanding medical device (2) and the radially self-expanding medical device (2) is collapsed within the sheath (11).

20 Claims, 21 Drawing Sheets

(51) Int. Cl.
*A61F 2/95* (2013.01)
*A61F 2/966* (2013.01)

(52) U.S. Cl.
CPC ....... *A61F 2/962* (2013.01); *A61F 2002/9511* (2013.01); *A61F 2002/9528* (2013.01); *A61F 2002/9665* (2013.01); *A61F 2250/0003* (2013.01)

(58) Field of Classification Search
CPC .......... A61F 2/962; A61F 2/966; A61F 2/954; A61F 2002/9522; A61F 2002/9528; A61F 2002/9534; A61F 2/2436; A61F 2/2439; A61F 2002/011
See application file for complete search history.

(56) References Cited

U.S. PATENT DOCUMENTS

| | | |
|---|---|---|
| 9,782,256 B2 | 10/2017 | Zeng et al. |
| 2004/0034363 A1 | 2/2004 | Wilson et al. |
| 2005/0113864 A1 | 5/2005 | Gandhi et al. |
| 2006/0009833 A1 | 1/2006 | Chobotov et al. |
| 2006/0276830 A1 | 12/2006 | Balgobin |
| 2007/0299422 A1 | 12/2007 | Inganas et al. |
| 2008/0051869 A1* | 2/2008 | Yribarren .......... A61M 25/1011 623/1.11 |
| 2008/0082165 A1 | 4/2008 | Wilson et al. |
| 2009/0312829 A1* | 12/2009 | Aoba .................. A61F 2/94 623/1.11 |
| 2010/0049313 A1 | 2/2010 | Alon |
| 2011/0313505 A1* | 12/2011 | McHugo .................. A61F 2/954 623/1.12 |
| 2013/0296999 A1* | 11/2013 | Burriesci .............. A61F 2/2436 623/1.11 |
| 2013/0338787 A1 | 12/2013 | Hopkins |
| 2014/0142621 A1 | 5/2014 | Masters et al. |
| 2014/0343670 A1* | 11/2014 | Bakis ................... A61F 2/2436 623/2.11 |
| 2017/0290661 A1 | 10/2017 | Von Segesser et al. |

FOREIGN PATENT DOCUMENTS

| | | |
|---|---|---|
| EP | 2745810 A1 | 6/2014 |
| EP | 3071151 | 7/2016 |
| WO | 2014/189977 A1 | 11/2014 |

OTHER PUBLICATIONS

International Preliminary Report on Patentability, Application No. PCT/EP2016/067336, dated Jan. 23, 2018.

* cited by examiner

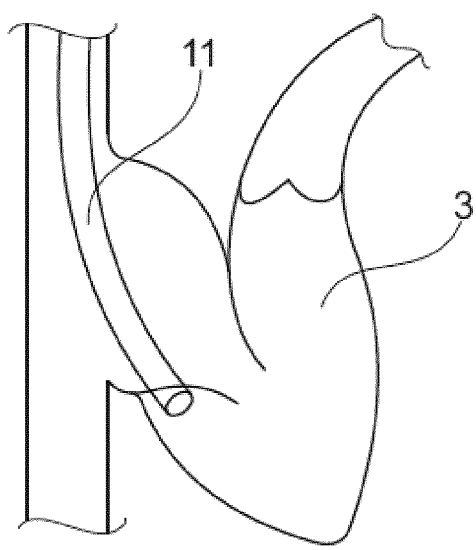 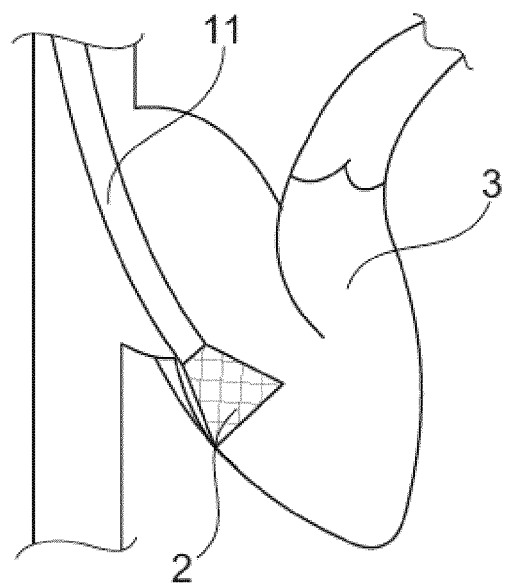
FIG. 19　　　　　　　　　　FIG. 20
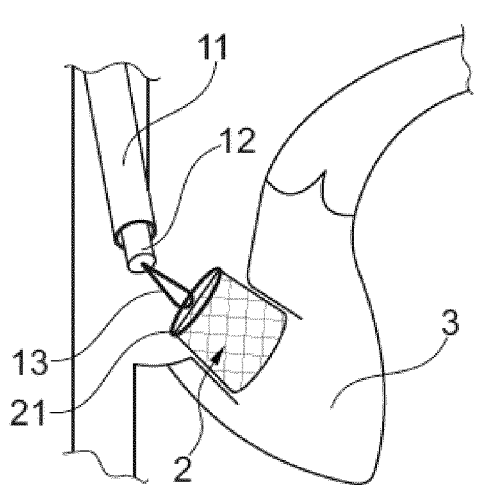 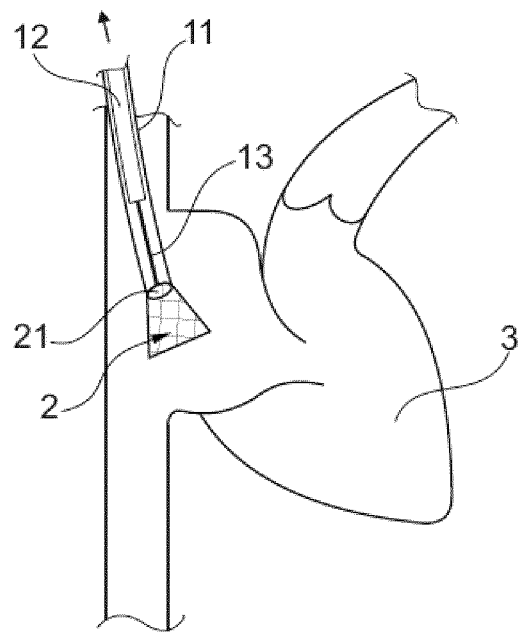
FIG. 21　　　　　　　　　　FIG. 22

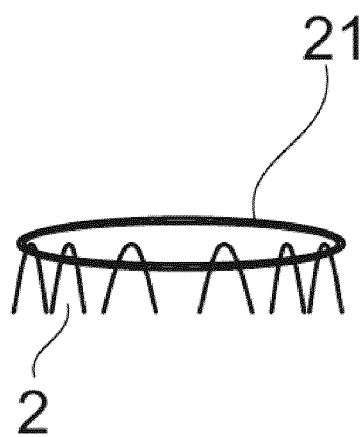
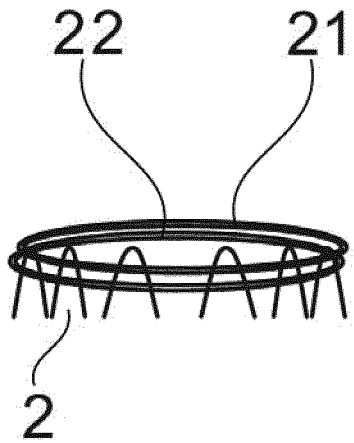
FIG. 38a  FIG. 38b
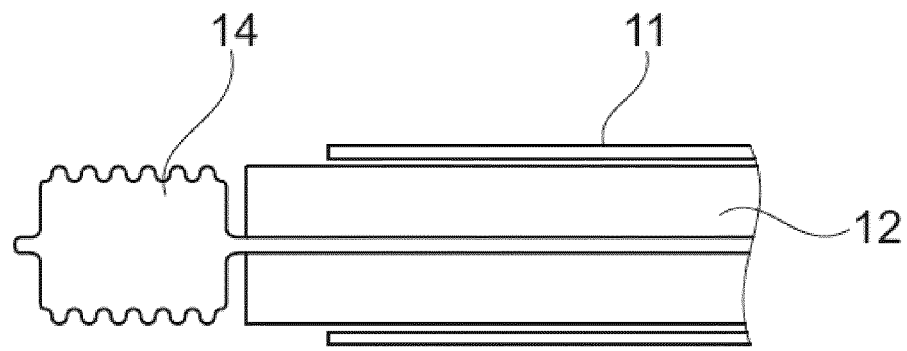
FIG. 39a
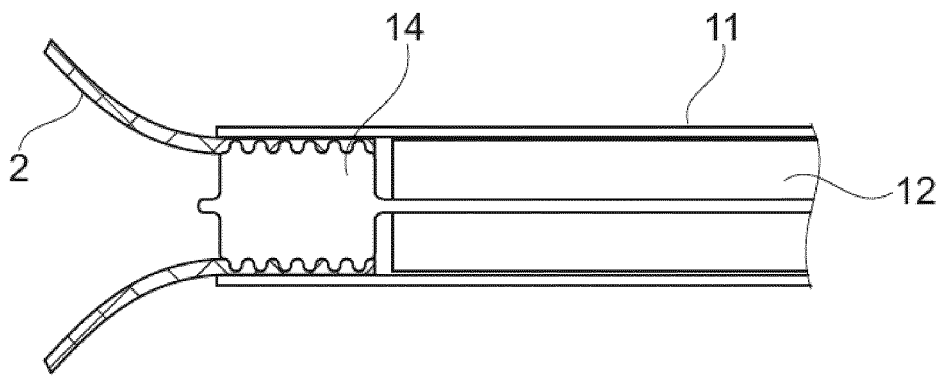
FIG. 39b

DELIVERY APPARATUS FOR SELF-EXPANDING MEDICAL DEVICE

FIELD OF INVENTION

The present invention pertains to the field of delivery apparatus for self-expanding medical device. In particular, the present invention relates to a delivery apparatus for radially self-expanding prosthetic heart valve.

BACKGROUND OF INVENTION

Valvular heart disease is recognized as a common disease in the elderly population. Mitral regurgitation—the mitral leaflets do not close properly leading to abnormal leaking of blood—is the most commonly occurring valve abnormality. Besides mitral regurgitation, conditions affecting the proper functioning of the mitral valve also include mitral valves stenosis—the opening of the mitral valve is narrowed leading to systolic function deterioration. Aortic valve, pulmonary valve and tricuspid valve may also be affected by regurgitation and stenosis.

Typically, treatment for heart valve regurgitation or stenosis involves either administration of diuretics and/or vasodilators to reduce the amount of blood flowing back, or surgical procedures for either repair or replacement of the heart valve. Less invasive approaches recently implemented involve percutaneous expandable prosthetic heart valves.

U.S. Pat. No. 5,840,081 discloses a trans-vascular technique developed for introducing and replacing the diseased native heart valve using a flexible catheter in a manner that is less invasive than open heart surgery. Said patent especially discloses a prosthetic heart valve mounted in a crimped state on the distal portion of a flexible catheter and advanced through a blood vessel of the patient until the apparatus reaches the implantation site. The prosthetic valve at the catheter distal end is then expanded to its functional size at the site of the defective native valve, such as by inflation or by self-expansion.

Among expandable prosthetic heart valves, self-expanding prosthetic valves are preferred for non-cylindrical frame because a balloon cannot conform to the specific shape of the frame. However one drawback associated with self-expanding device, relies in that, as the operator move the device to the distal end of the delivery sheath, the device tends to "jump" out in an uncontrolled manner from the distal open end of the delivery sheath. In fact, the partially deployed part of the frame exerts a biased outward force which tends to cause the self-expanding device to be ejected from the delivery sheath.

To address this issue, delivery apparatus with retaining mechanisms secured to the self-expanding prosthetic valves have been developed to avoid undesired "jump" out of the delivery sheath until exact positioning has been validated by the operator.

For instance, US 2010/0049313 discloses a delivery apparatus comprising a valve retaining mechanism. The valve is not disposed distally within the delivery sheath but said delivery sheath comprises a nose piece disposed at the distal end in order to avoid undesired positioning of the valve.

One drawback associated with delivery apparatus configured to control in a precise manner the delivery is that positioning is directly related to the delivery apparatus ability to precisely reach the implantation site. Complex steerable delivery apparatus, in addition to complex imaging technique, have to be used to precisely reach the implantation site.

Another drawback associated with delivery apparatus configured to controlled in a precise manner the delivery is that positioning of the prosthetic heart valve in the implantation site should be assess while the heart valve prosthesis is still partially deployed and retaining mechanism engaged. Displacement which could occur to balance the radial outward force of the heart valve prosthesis and the resistive and compressive radial force of the surrounding tissue when the retaining mechanism is removed is thus unknown and not controlled.

Moreover, the catheter, inserted in the vasculature, induce a remodeling of the implantation site, with associated mechanical stresses on the tissue and in the catheter.

During the deployment, the catheter is separated from the prosthesis and some mechanical stresses disappear suddenly. There is, at this moment, a movement between the catheter and the deployment position which can move out the prosthesis. For example, the angle between the internal jugular vein and the plan of the tricuspid ring is around 60° and the catheter have to bend and press the edge of the vessel to conform with this angle.

Furthermore, after implantation, the catheter, fixed to the surgeon and maintained by the vasculature, is mobile relative to the prosthesis just implanted in the native environment. Indeed, during the heartbeat, the catheter has no mobility while the tricuspid annular plane systolic excursion (TAPSE) can reach 20 mm. If the prosthesis is fixed to the catheter, this makes very difficult to the surgeon to avoid any impairment of the just implanted prosthesis by the catheter while keeping the ability to check properly the performance of the device and to retrieve the device in case of implantation failure.

U.S. Pat. No. 5,925,076 consists in a delivery apparatus wherein a collapsible artificial blood vessel is in a catheter. A tubular cover is connected to the distal part of an artificial blood vessel and pulls the artificial blood vessel outside the catheter. In the same way, the European patent application EP2745810 describes an apparatus for deployment of an implantable medical device including a stent graft and a restraining device, such as cord or suture, which holds the stent in a compressed configuration. Withdrawal of one or more trigger wires facilitates the release and allows the stent to become fully deployed within the vessel. The drawback of this background is that the medical device has to be deployed in a low motion area to reach the perfect desired location. Indeed, the holding to the proximal part or the body part of the medical device prevent a free-deployment of the medical device. Then, the implantation site should fit perfectly with the catheter. As explained above, these apparatus will be unable to deliver correctly a medical device in a relative moving heart.

Furthermore, the fully deployed prosthesis valve is not retrievable in the delivery sheath. Mispositioning, inefficiency or sized-mismatch cannot be corrected after the retaining mechanism has been removed. Some delivery apparatus attempt to address this issue such as for instance WO2012/052718. Said delivery apparatus comprises a sheath and a holder movable within the sheath and configured to constrain radially the prosthetic valve in order to enable removal of the prosthetic valve. However, the mechanism is complex and requires a larger diameter of the external sheath. Moreover, with said delivery apparatus, the prosthesis cannot be connected to the delivery apparatus by the surgeon in the operating room.

There is thus a need for an easy to use delivery apparatus enabling unrestrained deployment of a medical device, such as a prosthetic heart valve, and/or retrievability of the medical device once fully positioned. In particular, there is a need for a holding and retrieving mechanism and/or a retaining mechanism which may be easily connected to the medical device by the surgeon or an assistant in the operating room.

SUMMARY

The present invention consists in a delivery apparatus for delivering a radially self-expanding medical device having a proximal portion and a distal portion, said delivery apparatus comprising a radially self-expanding medical device comprising a proximal end and a distal end; an elongated tubular member having a proximal end, a distal end and a lumen extending along a longitudinal axis from the proximal end to the distal end; a sheath, said sheath being coaxially disposed around the elongated tubular member; wherein the elongated tubular member is movable relative to the sheath; wherein the sheath is configured for receiving the radially self-expanding medical device in a radially compressed state; and a holding and retrieving mechanism comprising a first end and a second end; the holding and retrieving mechanism being configured to constrain radially the proximal portion of the radially self-expanding medical device such that in response to a proximal movement of the elongated tubular member relative to the sheath, the holding and retrieving mechanism constrains radially the proximal portion of the radially self-expanding medical device and the radially self-expanding medical device is collapsed within the sheath; wherein the elongated tubular member comprises a first holding means for releasably holding the first end of the holding and retrieving mechanism near the distal end of the elongated tubular member, and a second holding means for holding the second end of the holding and retrieving mechanism near the distal end of the elongated tubular member; wherein the first holding means is configured for releasing the first end of the holding and retrieving mechanism by actuation of the first holding means at the proximal end of the elongated tubular member; and wherein the holding and retrieving mechanism is connected only to the proximal end of the radially self-expanding medical device.

In one embodiment, the holding and retrieving mechanism comprises a longitudinal axis and the ratio between the length along the longitudinal axis and the greater length in the transverse plane is greater than 3, preferably greater than 20, more preferably greater than 100.

In one embodiment, the first holding means comprises a first aperture and a second aperture through the elongated tubular member from the lumen to an outer wall, said first and second apertures being disposed near the distal end of the elongated tubular member and said first aperture being disposed proximally of said second aperture; and a trigger wire disposed within the lumen of the elongated tubular member; the trigger wire exits said lumen of said elongated tubular member through the first aperture and re-enters said lumen of said elongated tubular member through the second aperture such that said trigger wire forms a bend, said bend of said trigger wire engaging said first end of the holding and retrieving mechanism; said trigger wire being configured to be withdrawn in the proximal direction through said lumen of said elongated tubular member such that said trigger wire disengages said first end of the holding and retrieving mechanism.

In one embodiment, the first holding means is an elastic hook which holds one end of the holding and retrieving mechanism in an aperture near the distal end of the elongated tubular member.

In one embodiment, the first holding means are pliers configured to releasably hold the first end of the holding and retrieving mechanism.

In one embodiment, the first holding means comprises a coaxial element movable relative to the elongated member; which comprises a sharp window, wherein the inner edge of said sharp window comprises sharp means configured to cut the holding and retrieving mechanism, and wherein the holding and retrieving mechanism passes through the sharp window.

In one embodiment, the second holding means is configured for releasably holding the second end of the holding and retrieving mechanism and comprises a third aperture and a fourth aperture through the elongated tubular member from the lumen to an outer wall, said third and fourth aperture being disposed near the distal end of the elongated tubular member and said third aperture being disposed proximally of said fourth aperture; and a trigger wire disposed within the lumen of the elongated tubular member; the trigger wire exits said lumen of said elongated tubular member through the third aperture and re-enters said lumen of said elongated tubular member through the fourth aperture such that said trigger wire forms a bend, said bend of said trigger wire engaging said second end of the holding and retrieving mechanism; said trigger wire being configured to be withdrawn in the proximal direction through said lumen of said elongated tubular member such that said trigger wire disengage said second end of the holding and retrieving mechanism.

In one embodiment, the second holding means is configured for non-detachably holding the second end of the holding and retrieving mechanism and comprises a hook and the second end of the holding and retrieving mechanism comprises a loop configured to be hooked to the hook of the elongated tubular member.

In one embodiment, the second holding means is configured for non-detachably holding the second end of the holding and retrieving mechanism and comprises a through-hole in the elongated tubular member, wherein the second end of the holding and retrieving mechanism may be knotted to the elongated tubular member through said trough-hole.

In one embodiment, the second holding means is configured for non-detachably holding the second end of the holding and retrieving mechanism and comprises a recess having a shape complementary to the shape of the distal end of the holding and retrieving mechanism, said recess being configured for retaining the distal end of the holding and retrieving mechanism.

In one embodiment, the delivery apparatus further comprises a retaining mechanism configured for releasably retaining the radially self-expanding medical device within the sheath; said retaining mechanism comprising a first portion connected to the elongated tubular member and a second expandable portion disposed adjacent the distal end of the elongated tubular member and extending through the proximal portion of the radially self-expanding medical device, said second expandable portion being configured to expand from a collapsed profile to an expanded profile wherein the second expandable portion presses the proximal portion of the radially self-expanding medical device against the inner wall of the sheath so as to secured the radially self-expanding medical device therein; the second expandable portion exhibits a longitudinal flexibility.

In one embodiment, the second expandable portion of the retaining mechanism also comprises a balloon and the first portion of the retaining mechanism comprises a channel in fluid communication with the balloon for injecting a fluid into the balloon so as to expand the balloon.

In one embodiment, the second expandable portion comprises a flexible member comprising a proximal end and a distal end; and the first portion of the retaining mechanism comprises an actuator engaged with the distal end of the flexible member; wherein in response to a proximal movement of the actuator relative to the proximal end of the flexible member, the flexible member expands to the expanded profile.

In one embodiment, the proximal end of the flexible member is secured to the distal end of the elongated tubular member.

In one embodiment, the radially self-expanding medical device comprises a plurality of proximal apices disposed at a proximal end of the radially self-expanding medical device; and wherein the holding and retrieving mechanism engages at least one apex.

In one embodiment, the radially self-expanding medical device comprises a plurality of proximal apices disposed at a proximal end of the radially self-expanding medical device and a filament extending through the plurality of proximal apices; and wherein the holding and retrieving mechanism engages the filament.

In one embodiment, the radially self-expanding medical device comprises a radially collapsible and expandable heart valve prosthesis.

Definitions

In the present invention, the following terms have the following meanings:

As used herein the singular forms "a", "an", and "the" include singular and/or plural reference unless the context clearly dictates otherwise.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value or range within 20 percent, preferably within 10 percent of said given value or range.

The term "active" refers herein to a retaining mechanism which must be inactivated by manual actuation.

The term "inactive" refers herein to a retaining mechanism which may be inactivated by the sole respective positioning of the sheath and the elongated tubular member, without any manual actuation.

With regard to the terms "distal" and "proximal" within the present description, unless otherwise specified, the terms can reference a relative position of the portions of a medical device, a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter).

"Prosthetic heart valve" refers herein to mechanical, biological, textile, elastomeric or tissue-engineered heart valves designed to replicate the function of the natural valves of the human heart.

"Radial anchorage" refers herein to the anchorage of a prosthetic heart wall predominantly by the device radial expansion force.

"Resorbable" means herein susceptible to be absorbed or eliminated by a mammalian, preferably a human, through a physiological process.

"Flexible" means herein able to change it shape or able to be deformed easily.

"Elastic bending modulus" illustrates the tendency for a material to bend and is computed as the ratio of stress to strain in flexural deformation.

"Ultimate Tensile Strength" is the capacity of a material to withstand loads tending to elongate. The ultimate tensile strength is measured by the maximum stress that a material can withstand while being stretched or pulled before breaking.

"Anchoring device" refers herein to a self-expanding device designed for allowing the implantation and anchorage of a prosthetic heart valve in a mammalian heart.

"Anchoring system" refers herein to a system comprising the anchoring device, a prosthetic heart valve support and a prosthetic heart valve.

DETAILED DESCRIPTION

The following detailed description will be better understood when read in conjunction with the drawings. For the purpose of illustrating, the apparatus and system are shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly it should be understood that where features mentioned in the appended claims are followed by reference signs, such signs are included solely for the purpose of enhancing the intelligibility of the claims and are in no way limiting on the scope of the claims.

The present invention relates to a delivery apparatus for delivery of a radially self-expanding medical device, such as a prosthetic heart valve.

As depicted in FIG. 1, a delivery apparatus 1 comprises a sheath 11, an elongated tubular member 12 slidable within the sheath 11 and two handles; one 111 at the proximal end of the sheath 11 and one 121 at the proximal end of the elongated tubular member 12. The elongated tubular member 12 comprises a proximal end, a distal end and a lumen extending along a longitudinal axis from the proximal end to the distal end. The sheath 11 comprises a lumen extending from its proximal end to its distal end. The sheath 11 is coaxially disposed around the elongated tubular member 12 and the elongated tubular member 12 is movable relative to the sheath 11.

As depicted in FIG. 2, the sheath 11 is configured for receiving a radially self-expanding medical device 2 in a radially compressed state. In the crimped state (i.e. the radially compressed state), the medical device 2 is disposed adjacent to the distal end of the elongated tubular member 12 and is covered by the sheath 11.

The delivery apparatus 1 is configured to deliver a self-expanding medical device 2 from a collapsed state (see FIG. 2) to a deployed state (see FIGS. 4 and 5) by way of a partly deployed state (see FIG. 3).

As depicted in FIGS. 2 and 3, in order to deploy the medical device 2, the sheath 11 is slide relative to the elongated tubular member 12 to uncover the medical device 2. The medical device 2 may be pushed distally by the elongated tubular member 12 relative to the sheath 11.

As depicted in FIG. 3, when the sheath 11 is partially removed, the self-expanding medical device 2 is partially deployed. In the partially deployed position, the self-expanding medical device 2 projects partially distally from the sheath 11.

Once the medical device has been positioned—e.g. once a prosthetic heart valve has been positioned within the native heart valve—it may be useful to retrieve the said medical device, for instance due to malfunction. In order to enable retrieval of the medical device, the elongated tubular member is connected to the medical device, preferably to the proximal end of the medical device, by means of a holding and retrieving mechanism.

According to one embodiment, the holding and retrieving mechanism is connected to the proximal end of the radially self-expanding medical device.

According to one embodiment, the holding and retrieving mechanism is connected only to the proximal end of the radially self-expanding medical device.

Therefore, according to a first aspect, this invention relates to delivery apparatus for delivering a radially self-expanding medical device comprising a proximal portion and a distal portion, said delivery apparatus comprising:
  a radially self-expanding medical device comprising a proximal end and a distal end;
  an elongated tubular member comprising a proximal end, a distal end and a lumen extending along a longitudinal axis from the proximal end to the distal end;
  a sheath, said sheath being coaxially disposed around the elongated tubular member; wherein the elongated tubular member is movable relative to the sheath; and wherein the sheath is configured for receiving the radially self-expanding medical device in a radially compressed state; and
  a holding and retrieving mechanism; the holding and retrieving mechanism being configured to constrain radially the proximal portion of the radially self-expanding medical device such that in response to a proximal movement of the elongated tubular member relative to the sheath, the holding and retrieving mechanism constrains radially the proximal portion of the radially self-expanding medical device and the radially self-expanding medical device is collapsed within the sheath.

According to said first aspect, the elongated tubular member comprises a first holding means for releasably holding the first end of the holding and retrieving mechanism near the distal end of the elongated tubular member, and a second holding means for holding the second end of the holding and retrieving mechanism near the distal end of the elongated tubular member. The first holding means is configured for releasing the first end of the holding and retrieving mechanism by actuation of the first holding means at the proximal end of the elongated tubular member; and the holding and retrieving mechanism is connected only to the proximal end of the radially self-expanding medical device.

As depicted in FIGS. 4 and 5, the delivery apparatus 1 comprises a holding and retrieving mechanism 13 configured to be connected to self-expanding medical device 2.
  According to one embodiment,
  the holding and retrieving mechanism 13 comprises a first end 131 and a second end 132; and is configured to constrain radially the proximal portion of the radially self-expanding medical device 2 such that in response to a proximal movement of the elongated tubular member 12 relative to the sheath 11, the holding and retrieving mechanism 13 constrains radially the proximal portion of the radially self-expanding medical device 2 and the radially self-expanding medical device 2 is collapsed within the sheath 11; and
  the elongated tubular member 12 comprises a first holding means for releasably holding the first end of the holding and retrieving mechanism 131 at or near the distal end of the elongated tubular member 12, and a second holding means for holding the second end of the holding and retrieving mechanism 132 at or near the distal end of the elongated tubular member 12; and
  the first holding means is configured for releasing the first end of the holding and retrieving mechanism 131 by actuation of the first holding means at the proximal end of the elongated tubular member 12.

According to the Applicant, on the contrary to FIGS. 6 and 7, it is advantageous that the holding and retrieving mechanism 13 does not pass through the whole length of the lumen 122 of the elongated tubular member 12. If the holding and retrieving mechanism 13 does not pass through the whole length of the lumen 122 of the elongated tubular member 12, the medical device 2 may be easily connected to the delivery apparatus 1 by the surgeon or an assistant in the operating room.

The medical device 2 can be retrieve after the sheath 11 removal and the expansion of the medical device 2. This retrieving is made possible by a connection between the medical device 2 and the delivery apparatus 1 before, and after full deployment of the medical device 2.

According to the applicant, the holding and retrieving mechanism 13 is connected to the proximal part of the medical device 2. In the embodiment wherein the medical device 2 has a lumen 122, the holding and retrieving mechanism 13 is not connected and is not located in the lumen 122 of the medical device 2.

During the deployment, the behavior, expansion, and position of the medical device 2 are not limited by the delivery apparatus 1.

According to one embodiment, the length and/or the flexibility of holding and retrieving mechanism 3 is configured such that the holding and retrieving mechanism 13 does not restrain the deployment of the radially self-expanding medical device 2. According to one embodiment, unless relative sliding of the elongated tubular member 12 form the distal to the proximal end of the sheath 11, the holding and retrieving mechanism 13 apply and transmit no force to the medical device.

According to one embodiment, the length and/or the flexibility of holding and retrieving mechanism 13 is configured such that the holding and retrieving mechanism 13 does not remove any degree of freedom of the radially self-expanding medical device 2. For instance, for implantation at a native heart valve said radially self-expanding medical device is able and free to place itself between an upper chamber and a lower chamber, such as between an atrium and a ventricle.

According to one embodiment, when the self-expanding medical device 2 is removed from the sheath 11, the length of the holding and retrieving mechanism 13 is greater than twice the distance between the self-expanding medical device 2 and the distal part of the elongated tubular member 12 when the medical device 2 is on the desired localization.

According to one embodiment, when the self-expanding medical device 2 is deployed, the holding and retrieving mechanism 13 enables merely to retrieve the self-expanding medical device 2 in the sheath 11.

According to one embodiment, the holding and retrieving mechanism 13 is not a rigid bar.

According to one embodiment, the holding and retrieving mechanism 13 is flexible.

According to one embodiment as depicted in FIGS. 8 and 9, the first holding means comprises a first aperture 1231 and a second aperture 1232 through the elongated tubular member 12 from the lumen 122 to an outer wall, said first and second apertures 1231, 1232 being disposed near the distal end of the elongated tubular member 12 and said first aperture 1231 being disposed proximally of said second aperture 1232; and a trigger wire 1233 disposed within the lumen of the elongated tubular member 122; the trigger wire 1233 exits said lumen of said elongated tubular member 122 through the first aperture 1231 and re-enters said lumen of said elongated tubular member 122 through the second aperture 1232 such that said trigger wire 1233 forms a bend, said bend of said trigger wire 1233 engaging said first end of the holding and retrieving mechanism 131; said trigger wire 1233 being configured to be withdrawn in the proximal direction through said lumen of said elongated tubular member 122 such that said trigger wire 1233 disengages said first end of the holding and retrieving mechanism 131.

According to one embodiment, the trigger wire is a synthetic or natural wire, preferably a metallic wire. According to one embodiment, the trigger wire is a yarn, filament or multifilament with or without treatment. The trigger wire is preferably a nitinol wire with lubricant coating.

According to one embodiment as depicted in FIG. 10, the first end of the holding and retrieving mechanism 131 comprises a closed loop. According to one embodiment, the second end of the holding and retrieving mechanism 132 comprises a closed loop.

According to one embodiment, as depicted in FIG. 31 the second holding means is configured for releasably holding the second end of the holding and retrieving mechanism 132 and comprises a third aperture 1245 and a fourth aperture 1244 through the elongated tubular member 12 from the lumen 122 to an outer wall, said third and fourth aperture being disposed near the distal end of the elongated tubular member 12 and said third aperture 1245 being disposed proximally of said fourth aperture 1244; and a trigger wire 1238 disposed within the lumen of the elongated tubular member 122; the trigger wire 1238 exits said lumen of said elongated tubular member 122 through the third aperture 1245 and re-enters said lumen of said elongated tubular member 122 through the fourth aperture 1244 such that said trigger wire 1238 forms a bend, said bend of said trigger wire 1238 engaging said second end of the holding and retrieving mechanism; said trigger wire 1238 being configured to be withdrawn in the proximal direction through said lumen of said elongated tubular member 122 such that said trigger wire 1238 disengage said second end of the holding and retrieving mechanism 132. According to one embodiment, the elongated tubular member 12 comprises a first lumen for the trigger wire of the first holding means and a second lumen for the trigger wire of the second holding means. According to one embodiment, as depicted FIG. 31 the elongated tubular member 12 comprises a single lumen 122 and the first and second trigger wires of respectively the first and second holding means are disposed within the said lumen.

According to one embodiment, the technical solution to release or recapture the holding and retrieving mechanism is not a trigger wire.

According to one embodiment, as depicted for instance in FIGS. 43*a* and 43*b*, the first holding means comprises a coaxial element movable relative to the elongated member (12) which comprises a sharp window 1237. The inner edge of said sharp window comprises sharp means. The holding and retrieving mechanism passes through the sharp window 1237. Once the medical device is well located and before the removal of the catheter, a relative movement of the coaxial element regarding the elongated member cut the holding and retrieving mechanism (FIG. 43*b*). The distal extremity of the coaxial element does not comprise sharp means in order to not remove the second end of the holding and retrieving mechanism The sheath 11 is not illustrated on these figures.

According to one embodiment as depicted for instance in FIGS. 42*a* and 42*b*, the first holding means is an elastic hook 1235 which holds one end of the holding and retrieving mechanism in an aperture 1236.

In said embodiment, the elastic hook has an inner part secured in the elongated member 12 and an outer part outside the elongated member 12. When the distal part of the elongated member 12 secured with the elastic hook 1235 is in the sheath 11, the outer part is maintain sensibly parallel to proximal direction of the sheath, between the elongated member 12 and the sheath 11. In this position, the extremity of the outer part of the elastic hook fits together in an aperture 1236 and maintains the holding and retrieving mechanism 13 (see FIG. 42*a*). When the distal part of the elongated member 12 is out of the sheath 11, the elastic hook 1235 is taking its equilibrium shape (without stresses), and the extremity get out of the aperture 1236, releasing the holding and retrieving mechanism 13 (see FIG. 42*b*).

According to one embodiment, as depicted FIGS. 44*a* and 44*b*, the means for holding the first end of the holding and retrieving mechanism are pliers 1234. The first end of the holding and retrieving mechanism comprises a loop and the pliers 1234 catch the loop for maintaining the holding and retrieving mechanism 13. Such pliers can be activated from the proximal extremity of the catheter by the surgeon or the operator and enable to release the holding and retrieving mechanism (FIG. 44*b*).

According to one embodiment, as depicted in FIG. 11, the second holding means is configured for non-detachably holding the second end of the holding and retrieving mechanism 132 and comprises a hook 1241 and the second end of the holding and retrieving mechanism 132 comprises a loop configured to be hooked to the hook 1241 of the elongated tubular member 12.

According to one embodiment, as depicted in FIG. 12, the second holding means is configured for non-detachably holding the second end of the holding and retrieving mechanism 132 and comprises a recessed hook 1241 having a shape complementary to the shape of the distal end of the holding and retrieving mechanism 132, said recess 1243 being configured for retaining the distal end of the holding and retrieving mechanism 132. According to one embodiment, the second end of the holding and retrieving mechanism 132 comprises a distal part having a shape complementary to the shape of the recessed hook 1241, so that said recessed hook 1241 retains the distal end of the holding and retrieving mechanism 132.

According to one embodiment, as depicted in FIG. 13, the second holding means is configured for non-detachably holding the second end of the holding and retrieving mechanism 132 and comprises a through-hole 1242 (i.e. from the outer wall to the outer wall of the elongated tubular member 12) and wherein the second end of the holding and retrieving mechanism 132 may be knotted to the elongated tubular member 12 through said trough-hole 1242. According to one embodiment, the second holding means is configured for non-detachably holding the second end of the holding and retrieving mechanism 132 and comprises a substantially radially extending through-hole 1242; and wherein the second end of the holding and retrieving mechanism 132 may be knotted to the elongated tubular member 12 through said trough-hole 1242.

According to one embodiment, as depicted in FIG. 14, the second holding means is configured for non-detachably holding the second end of the holding and retrieving mechanism 132 and comprises a recess 1243 having a shape complementary to the shape of the distal end of the holding and retrieving mechanism 132, said recess 1243 being configured for retaining the distal end of the holding and retrieving mechanism 132. According to one embodiment, the second end of the holding and retrieving mechanism 132 comprises a distal part or protrusion having a shape complementary to the shape of the recess 1243, so that said second end of the holding and retrieving mechanism 132 closely fits within the said recess 1243 and said recess retains the distal end of the holding and retrieving mechanism 132. According to one embodiment, the protrusion cannot leave the recess 1243 when the sheath 11 covers the recess 1243.

According to one embodiment, the first holding means for releasably holding the first end of the holding and retrieving mechanism 131 and a second holding means for holding the second end of the holding and retrieving mechanism 132 are located at the same height along the longitudinal axis of the elongated tubular member 12. According to one embodiment, the first holding means for releasably holding the first end of the holding and retrieving mechanism 131 and a second holding means for holding the second end of the holding and retrieving mechanism 132 are not located at the same height along the longitudinal axis of the elongated tubular member 12. According to one embodiment, the first and second openings 1231, 1232 of the elongated tubular member 12 (dedicated to the trigger wire 1233 are located more distally than the second holding means for holding the second end of the holding and retrieving mechanism 132.

According to one embodiment holding and retrieving mechanism 13 comprises a longitudinal axis and the ratio between the length along the longitudinal axis and the greater length in the transverse plane is greater than 3, preferably greater than 20, and more preferably greater than 100. According to one embodiment, the ratio between the length along the longitudinal axis and the greater length in the transverse plane is greater than 5, 6, 7, 8, 9, 10, 15, 20, 25, 30, 35, 40, 50, 60, 70, 75, 80, 90, 100 or 150. The greater length in the transverse plane is the diameter or the width depending of the shape of the holding and retrieving mechanism.

According to one embodiment, the holding and retrieving mechanism 13 is a wire. According to one embodiment, the holding and retrieving mechanism 13 is a wire having a length between the distal end of the elongated tubular member 12 and the proximal end of the medical device 2 ranging from 1.5 to 3 times the length of the medical device. According to one embodiment, the holding and retrieving mechanism 13 is a wire having a length between the distal end of the elongated tubular member 12 and the proximal end of the medical device 2 ranging from 1 cm to 20 cm, preferably from 2 cm to 10 cm, and more preferably from 4 cm to 8 cm. According to the Applicant, the length and the flexibility of the wire enables full deployment of the medical device 2, such as a prosthetic heart valve, without constraint from the holding and retrieving mechanism 13.

According to one embodiment, the holding and retrieving mechanism is a wire configured such as the distance between the medical device and the distal extremity of the elongated member or the delivery system is ranging from 1 cm to 10 cm, and is preferably ranging from 4 cm and 7 cm.

According to one embodiment, the wire is round or a ribbon wire.

The holding and retrieving mechanism 13 is able to retrieve the fully deployed medical device 2. According to one embodiment, the holding and retrieving mechanism 13 has an ultimate tensile strength which should be greater than 200 MPa, preferentially greater than 500 MPa, and more preferentially greater than 1 GPa. According to one embodiment, said ultimate tension strength is 200 MPa, 250 Mpa, 500 MPa, 600 MPa, 700 MPa, 800 MPa, 900 MPa, 1 GPa, or 2 GPa.

According to one embodiment, the holding and retrieving mechanism 13 has an elastic bending modulus which should be lower than 2 GPa, preferentially lower than 0.4 GPa. According to one embodiment, the holding and retrieving mechanism 13 has an elastic bending modulus ranging from 0.1 GPa to 2 GPa.

According to one embodiment, the wire is a synthetic or natural wire. According to one embodiment, the wire is a metallic wire. According to one embodiment, the wire is in Nitinol or in stainless steel. According to one embodiment, the wire is a yarn, a filament or a multifilament with or without treatment. According to one preferred embodiment, the wire is a braided polyester yarn with lubricant coating. According to one embodiment, the holding and retrieving mechanism 13 is biocompatible. According to one embodiment, the holding and retrieving mechanism 13 is resorbable. According to one embodiment, the holding and retrieving mechanism 13 is non-resorbable. According to one embodiment, the holding and retrieving mechanism 13 is soaked with a substance in order to improve biological properties or/and mechanical properties such as a coating or an impregnation of silicone/Polytetrafluoroethylene.

According to one embodiment, the wire is a braided or a woven structure.

According to one embodiment, as depicted in FIGS. 9 to 18, the wire extends around and through the proximal end of the medical device 2.

According to one embodiment, as depicted for instance in FIG. 9, the holding and retrieving mechanism 13 is a wire forming a loop.

According to one embodiment, as depicted for instance in FIG. 10, the holding and retrieving mechanism 13 comprises a single wire and a loop at one of its ends.

According to one embodiment, the two ends of the holding and retrieving mechanism are connected to the distal end of the elongated member to give a loop. The holding and retrieving mechanism can also be connected to an element more distal than the distal end of the elongated member. The loop is connected to the proximal part of the medical device. According to said embodiment, the wire doesn't pass along the elongated member from the operator to the prosthesis in the implantation site.

Relative sliding of the elongated tubular member 12 from the distal end to the proximal end of the sheath 11 straightened the holding and retrieving mechanism 13 which drawn the head of the medical device 2 into the sheath 11. According to one embodiment, by pulling on the holding and retrieving mechanism 13 or by retracting the elongated tubular member 12, connected to the holding and retrieving mechanism 13, the holding and retrieving mechanism 13 cinches the proximal end of the medical device 2. The cinching reduces the diameter of the proximal end; thereby enabling retrieval. Relative sliding of the elongated tubular member 12 from the distal end to the proximal end of the sheath 11 forces to collapse the head of the medical device and drawn the medical device into the sheath 11.

The elongated member 12 is used to maintain, and/or release the holding and retrieving mechanism 13 and could be used, if needed, after the medical device 2 is fully deployed outside the sheath 11.

According to one embodiment, the holding and retrieving mechanism 13 enables the medical device re-entry in the sheath 11.

According to one embodiment, the holding and retrieving mechanism 13 enables the medical device to be repositioned by pulling on the holding and retrieving mechanism 13.

According to one embodiment, the elongated member 12 enables to push the medical device 2 outside the catheter in its proximal part and.

According to one embodiment, the elongated member 12 is not used for pushing the medical device. In said embodiment, dimensions of the elongated member are independent of the dimensions of the medical device.

According to said embodiment, as depicted in FIG. 45, the elongated member 12 is not in contact with the medical device 2 and, the elongated member is not used for pushing the medical device outside the sheath. In said embodiment, the retaining mechanism is used for the deployment of the medical device 2.

According to one embodiment, the deployment and implantation of the prosthetic heart valve comprise the following steps, as depicted in FIGS. 32*a*-32*g*:
- the medical device 2 is in collapsed state, connected to retaining and holding and retrieving mechanisms 14 and 13 of a delivery apparatus according to one embodiment (FIG. 32*a*),
- the medical device 2 is partially deployed and maintained by means of a retaining mechanism 14 (FIG. 32*b*). It is not necessary that the axial direction of the medical device correspond to the axial direction wherein the medical device will be implanted.
- the retaining mechanism 14 is released (FIG. 32*c*),
- the medical device 2 jumped (FIG. 32*d*) and is fully deployed (FIG. 32*e*). The medical device 2 has a high degree of freedom relative to delivery system,
- the holding and retrieving mechanism 13 is released by pulling out the trigger wire 1233 (FIG. 32*f*),
- the delivery apparatus is pulled out and the holding and retrieving mechanism 13 is withdrawn from the medical device head (FIG. 32*g*).

According to one embodiment, the retrieval of the radially self-expanding medical device 2 from a fully deployed state comprises the following steps, as depicted in FIGS. 15 to 18:
- the medical device is retained by the holding and retrieving mechanism 13 connected to the elongated tubular member 12 of a delivery apparatus 1 according to one embodiment of the present invention,
- the elongated tubular member 12 is pulled out in the proximal direction until the medical device is in contact with the sheath 11,
- the elongated tubular member 12 is pulled out in the proximal direction and the holding and retrieving mechanism 13 collapsed the medical device's head,
- the elongated tubular member 12 is pulled out in the proximal direction and the medical device enters fully within the sheath.

According to one embodiment, an additional coaxial sheath 16 is used around the delivery sheath 11, as depicted in FIGS. 46*a*-46*e*. According to one embodiment, said coaxial sheath 16 helps to cinch the medical device 2, either by strengthening the sheath 11 (see FIG. 46*c*) or by providing a first step of crimping with a larger diameter.

According to one embodiment, the sheath 11 is not the external sheath of the delivery device.

According to one embodiment, the coaxial sheath 16 could be one of the used medical devices during implantation, such as vascular system introducer which aims to puncture the vessel and offers a protecting open access for the delivery system to the vessel.

Before deployment, it may also be useful to prevent undesired deployment of the medical device by means of retaining mechanism.

Therefore, according to a second aspect, this invention relates to delivery apparatus for delivering a radially self-expanding medical device comprising a proximal portion and a distal portion, said delivery apparatus comprising:
- an elongated tubular member comprising a proximal end, a distal end and a lumen extending along a longitudinal axis from the proximal end to the distal end;
- a sheath, said sheath being coaxially disposed around the elongated tubular member; wherein the elongated tubular member is movable relative to the sheath; and wherein the sheath is configured for receiving the radially self-expanding medical device in a radially compressed state; and
- a retaining mechanism configured for releasably retaining the radially self-expanding medical device within the sheath.

According to one embodiment, the retaining mechanism 14 is releasable by actuation from the proximal end of the delivery apparatus 1. Release of the retaining mechanism 14 at a desired step allows jumping, free positioning, and self-positioning of the medical device.

According to one embodiment, the retaining mechanism exhibits a longitudinal flexibility configured so that the retaining mechanism does not restrain the longitudinal deployment of the radially self-expanding medical device.

According to said embodiment, the retaining mechanism 14 comprises a first portion connected to the elongated tubular member 122 and a second expandable portion 141 disposed adjacent the distal end of the elongated tubular member 12 and extending through the proximal portion of the radially self-expanding medical device 2, said second expandable portion being configured to expand from a collapsed profile to an expanded profile wherein the second expandable portion 141 presses the proximal portion of the radially self-expanding medical device 2 against the inner wall of the sheath 11 so as to secured the radially self-expanding medical device 2 therein. According to one embodiment, the first portion of the retaining mechanism 14 extends through the lumen of the elongated tubular member 122.

According to one embodiment, the retaining mechanism 14 is inactive when the sheath does not cover the medical device 2 (to avoid that the medical device be restrained at the full deployment step). According to said embodiment, as depicted for instance in FIG. 23, the retaining mechanism comprises a first portion extending through the lumen of the elongated tubular member 122 and a second expandable portion 141 disposed adjacent the distal end of the elongated tubular member 12 and extending through the proximal portion of the radially self-expanding medical device 2, said second expandable portion being configured to expand from a collapsed profile to an expanded profile wherein the second expandable portion 141 presses the proximal portion of the radially self-expanding medical device 2 against the inner wall of the sheath 11 so as to secured the radially self-expanding medical device 2 therein.

According to one embodiment, the second expandable portion 141 does not extend through the distal portion of the radially self-expanding medical device 2.

According to one embodiment, the second expandable portion 141 exhibits a longitudinal flexibility configured so that that the retaining mechanism 14 does not restrain the longitudinal deployment of the radially self-expanding medical device 2.

According to one embodiment as depicted in FIGS. 23 and 24, the second expandable portion 141 comprises a balloon and the first portion comprises a channel in fluid communication with the balloon for injecting a fluid into the balloon so as to expand the balloon. When the balloon is inflated, exerting a radial force from the inner side of the medical device 2 against the sheath 11, the medical device 2 is restrained and maintained within the sheath 11; when the balloon is deflated, the medical device 2 may jump out of the sheath 11 and may be fully deployed outside of the sheath 11.

According to one alternative embodiment, the second expandable portion 141 comprises a plurality of balloon (e.g. 2, 3, 4 or 5 balloons) connected together in series or in parallel with the first portion.

According to one embodiment, the second expandable portion 141 comprises a flexible member comprising a proximal end and a distal end; and the first portion comprises an actuator 142 engaged with the distal end of the flexible member; wherein in response to a proximal movement of the actuator 142 relative to the proximal end of the flexible member, the flexible member expands to the expanded profile.

According to one embodiment, the retaining mechanism 14 is located in the distal portion of the sheath 11 in the aim to increase the friction ratio between the medical device 2 and the sheath 11. It is a passive mechanism. In said embodiment, the retaining mechanism 14 could not be activated or deactivated from an actuator or from the proximal part of the catheter. However, in said embodiment, the retaining mechanism 14 has the ability to:

being automatically deactivated when the sheath 11 is not in contact with the medical 2 device anymore,
not disturbing the medical device 2 during the retrieving.

FIGS. 39a and 39b illustrate a first embodiment of the retaining mechanism 14 wherein the retaining mechanism 14 has a rough surface. This rough surface comprises a surface structure. When the medical device 2 is between the sheath 11 and the retaining mechanism 14, the surface structure (such as teeth) slightly distort the medical device 2 which takes the negative shape of the retaining mechanism 14. Thereby, the medical device 2 is strongly anchored to the retaining mechanism 14.

In an alternative embodiment, the shape of the medical device already has the negative shape of the retaining mechanism 14 such as to engage the surface structure of the retaining mechanism to increase the anchoring force.

FIGS. 40a and 40b illustrate a second embodiment of the retaining mechanism 14 made of an elastic component. The diameter of the elastic component has a diameter equal or greater than the sheath diameter in order to retain the medical device 2 when the retain mechanism 14 is in the sheath 11 with the medical device 2. In said embodiment, the retaining mechanism 14 pushes the medical device 2 against the sheath 11. The friction between the medical device 2 and the sheath 11 is such that it retains the medical device 2 within the sheath 11.

According to another embodiment, the two latter embodiments of the retaining mechanism (FIGS. 39a and 40a) are combined. The retaining mechanism 14 is an elastic and compressible component and comprises a rough surface. So, the medical device is retained by the force with the sheath and with the retaining mechanism.

According to one embodiment, the proximal end of the flexible member is connected to the distal end of the elongated tubular member 12. According to an alternative embodiment, the proximal end of the flexible member is configured to abut against the distal end of the elongated tubular member 12.

According to one embodiment, as depicted in FIGS. 25 and 26, the flexible member comprises a tubular portion having a longitudinal axis, the said portion having at least 2 longitudinal slots; preferably said slots are diametrically opposed. According to one embodiment, the tubular portion comprises at least 4 longitudinal slots, preferably regularly disposed around the tubular portion. When pulling on the actuator 142, the tubular portion extends outwardly, thereby exerting a radial force from the inner side of the medical device 2 against the sheath 11; the medical device 2 is thus restrained and maintained within the sheath 11. When pushing on the actuator, the tubular portion is flattened; the medical device 2 may thus be fully deployed outside of the sheath 11. According to one alternative embodiment, the second expandable portion 141 comprises a plurality of tubular portions having at least 2 longitudinal slots connected together in series.

According to one embodiment, as depicted in FIGS. 27 and 28, the flexible member comprises a helical flexible member. When pulling on the actuator 142, the helical flexible member extends outwardly, thereby exerting a radial force from the inner side of the medical device 2 against the sheath 11; the medical device 2 is thus restrained and maintained within the sheath 11. When pushing on the actuator, the helical flexible member is flattened; the medical device 2 may thus be fully deployed outside of the sheath 11. According to one alternative embodiment, the second expandable portion 141 comprises a plurality of helical flexible members.

According to one embodiment, the second expandable portion 141 comprises, arranged in series, a plurality of flexible members and/or balloons (e.g. an expandable balloon and a helical flexible member).

According to one embodiment, the retaining mechanism 14 is inactive when the distal end of the elongated tubular member 12 is located near the distal end of the sheath 11 (to avoid that the medical device be restrained at the full deployment step). According to said embodiment, as depicted in FIGS. 29 and 30, said retaining mechanism 14 comprises a plurality of wires 143 extending through the lumen of the elongated tubular member 122 and wherein each wire 143 comprises a distal end that is coiled for engagement with the proximal portion of the medical device 2. According to on embodiment, each coil comprises at least one complete winding of wire. According to one embodiment, the proximal end of said plurality of wires 143 is connected to the sheath and said plurality of wires 143 have a length configured such that, when uncoiled, the plurality of wires 143 does not project distally from the sheath 11. According to an alternative embodiment, by pulling out on the wires, the coils may be disengaged and the medical device 2 may be fully deployed outside of the sheath 11.

According to one embodiment, the retaining mechanism 14 is active. According to said embodiment, the retaining mechanism 14 is at least one trigger wire. According to one embodiment, the elongated tubular member 12 comprises a lumen 122 and, near the distal end, a first opening and a second opening, the second opening being positioned distally from the first opening. A trigger wire is disposed within the elongated tubular member 12, exits the lumen through the first opening and reenters through the second opening. The wire between the first and second opening may engage the proximal end of a medical device, preferably the mesh of a prosthetic heart valve. The trigger wire is configured to be withdrawn in the proximal direction through the lumen of the elongated tubular member 122 in order to deliver the medical device. According to one embodiment, the trigger wire is not resorbable.

According to one embodiment, the delivery apparatus is also used to collapse and load the medical device within the distal portion of the sheath.

According to one embodiment, the medical device is a prosthetic heart valve comprises a double wall comprising an inner wall and an outer wall.

According to one embodiment, the connection of the medical device to the holding and retrieving mechanism comprises the following steps, as depicted in FIGS. 33a-33b:
the holding and retrieving mechanism 13 is a flexible wire. One looped end of the wire is connected to the elongated member with a trigger wire 1233. The other end of the retaining wire 132 is free,
the free end of the retaining wire 13 cross the filament and is connected, by the surgeon or the operator, to the elongated member 12 with fitting mean.

According to the depicted embodiment, the medical device is loaded/crimped within the sheath with a double wall.

According to one embodiment, the elongated member 12 is pulled out in proximal direction until medical device inner part is collapsed within the sheath 11 for loading the medical device, as depicted in FIGS. 34a-34b. According to the depicted embodiment, the medical device is loaded/crimped within the sheath with a double wall.

According to one embodiment, as depicted in FIGS. 35a-35b, an external coaxial and slightly larger sheath 16 help to collapse the outer wall of the medical device in a double wall crimped configuration for loading the medical device. Preferably, the external sheath 16 has a flared distal end. In said embodiment, the holding and retrieving mechanism 13 is only used for its ability to apply tension on the head of the medical device 2 and retrieve said medical device 2. According to said embodiment, the medical device is loaded/crimped within the sheath with the double wall.

According to one embodiment, the load of a medical device 2 comprises the following steps, as depicted in FIGS. 36a-36c:
the medical device 2 is pre-compressed in a tubular support 17 and connected to the holding and retrieving mechanism 13,
the medical device is transferred from the tubular support 17 to the sheath 11, and
the retaining mechanism 14 is activated.

According to the depicted embodiment, the medical device is loaded/crimped within the sheath with a double wall.

According to one embodiment, the proximal end of the medical device 2 comprises at least two filaments. A first filament 21 is used to crimp the medical device 2 and is removed from the medical device 2 before loading in the catheter. The second filament 22 is used to connect the medical device 2 to the elongated member 12 by means of a holding and retrieving mechanism 13 (see FIGS. 37a-37c). According to one embodiment, the same holding and retrieving mechanism 13 is used for loading the medical device and for retrieval of the medical device 2. According to one embodiment, two different holding and retrieving mechanisms are used on the same elongated member for loading the medical device 2 and for retrieval of the medical device 2. According to one embodiment, two different catheters are used for loading the medical device and for retrieval of the medical device 2.

According to a third aspect, this invention relates to a delivery apparatus according to anyone of the embodiments of the first aspect and further comprising a retaining mechanism according to anyone of the embodiments of the second aspect.

According to one embodiment, the retaining mechanism 14 and the holding and retrieving mechanism 13 are separated mechanisms.

According to one embodiment, the elongated tubular member 12 comprises a single lumen 122. According to an alternative embodiment, the elongated tubular member 12 comprises at least two lumina: at least one lumen is dedicated to the holding and retrieving mechanism 13 and at least one lumen is dedicated to the retaining mechanism 14.

According to a fourth aspect, the invention relates to a delivery system 4 for delivering a radially self-expanding medical device 2 comprising a delivery apparatus 1 according to the present invention and a radially self-expanding medical device 2.

According to one embodiment, at least one part of the holding and retrieving mechanism engages/is connected to the radially self-expanding medical device 2. According to one embodiment, the holding and retrieving mechanism is a wire and at least one part of the wire engages/is connected to the radially self-expanding medical device 2.

According to one embodiment, the radially self-expanding medical device 2 comprises a plurality of proximal apices disposed at a proximal end of the radially self-expanding medical device 2; and wherein the holding and retrieving mechanism 13 engages at least one apex.

According to one embodiment, the radially self-expanding medical device 2 comprises a plurality of proximal apices disposed at a proximal end of the radially self-expanding medical device 2 and a filament 21 extending through the plurality of proximal apices; and wherein the holding and retrieving mechanism 13 engages the filament 21.

Interlacing pattern of filament allows complete and uniform head medical device crimping. Each filament 21 could have different interlacing pattern. Preferably, interlacing pattern minimizes friction between filament 21 and medical device struts or apices.

According to one embodiment, the filament 21 is a synthetic or natural filament. According to one embodiment, the filament is a metallic filament 21. Preferably, the filament 21 is a braided polyester yarn with lubricant coating. According to one embodiment, the filament 21 is resorbable. According to one embodiment, the filament 21 is non-resorbable. Relative sliding of the elongated tubular member 12 from the distal end to the proximal end of the sheath 11 straightened the holding and retrieving mechanism 13. The holding and retrieving mechanism 13 then straightened the filament 21 which forces to collapse and crimp the head of the medical device and draw the medical device into the sheath 11.

According to one embodiment, one end of the holding and retrieving mechanism 13 is manually interlaced or engaged with the medical device before being firmly connected at or near the distal end of the elongated tubular member 12. According to one embodiment, one end of the holding and retrieving mechanism 13 is manually interlaced or engaged in a releasable way with the medical device before being firmly connected at or near the distal end of the elongated tubular member 12. According to a preferred embodiment, one end of the holding and retrieving mechanism 13 could be manually interlaced or engaged in a reversible way with the medical device before being firmly connected at the distal end of the elongated member 12.

According to one embodiment, the holding and retrieving mechanism 13 is releasable secured to the elongated member 12. According to one embodiment, one end of the holding and retrieving mechanism 13 is secured in a non-detachable manner to the elongated member 12.

According to one embodiment, the proximal end of the medical device 2 comprises one filament 21 (see FIG. 38*a*) or a plurality of filaments 21, 22 (see FIG. 38*b*).

According to the Applicant it is advantageous if the interlacing between the holding and retrieving mechanism 13 and the medical device is minimized in order to avoid friction and thus migration or dislodgement during removal of the retaining mechanism 13. It is also advantageous if the wire of the holding and retrieving mechanism 13 does not pass through the elongated tubular member 12 in order to avoid friction and thus migration or dislodgement during removal of the retaining mechanism 13.

According to one embodiment as depicted in FIGS. 19 to 22, the radially self-expanding medical device 2 comprises radially collapsible and expandable heart valve prosthesis. According to one embodiment, the radially self-expanding medical device 2 consists of radially collapsible and expandable heart valve prosthesis. In said embodiment, the delivery system 4 is configured for advancing a prosthetic heart valve through vasculature of a heart 3 for replacing a diseased native valve. According to one embodiment, the expandable heart valve prosthesis comprises a prosthetic heart valve and an anchoring device. Said anchoring device is configured for anchoring the prosthetic heart valve within the native valve.

According to one embodiment, at least one end of the holding and retrieving mechanism 13 is releasable.

According to one embodiment, at least one end of the holding and retrieving mechanism 13 is releasable by the operator from the proximal part of the elongated member 12. According to one embodiment, at least one end of the holding and retrieving mechanism 13 is releasable by actuation from the proximal end of the apparatus.

According to one embodiment, one releasable end of the holding and retrieving mechanism 13 is freely removed from the filament 21 at the proximal part of the medical device 2. According to one embodiment, the holding and retrieving mechanism 13 is releasable in such way that the wire/loop is freely disconnected from the medical device 2 upon relative sliding of the elongated member 12 in proximal direction. No force affects or dislodges the medical device 2.

According to one embodiment, one end of the holding and retrieving mechanism 13 is releasable secured to the elongated member 12, for instance by means of a trigger wire 1233. According to one embodiment, the trigger wire 1233 is not resorbable.

According to one embodiment as depicted in FIGS. 41*a*, 41*b* and 41*c*, the medical 2 device can be load in the sheath 11 using cone shape 15. On one embodiment, the sheath 11 is not the catheter sheath. On said embodiment, the external sheath 16 can be removed after the medical device loading and before introducing the delivery system in the patient body.

While various embodiments have been described and illustrated, the detailed description is not to be construed as being limited hereto. Various modifications can be made to the embodiments by those skilled in the art without departing from the true spirit and scope of the disclosure as defined by the claims.

BRIEF DESCRIPTION OF THE DRAWINGS

FIG. 15: the medical device 2 is retained by the holding and retrieving mechanism 13 connected to the elongated tubular member 12 of a delivery apparatus 1 according to one embodiment;

FIG. 16: the elongated tubular member 12 is pulled out in the proximal direction until the medical device 2 is in contact with the sheath 11;

FIG. 17: the elongated tubular member 12 is pulled out in the proximal direction and the holding and retrieving mechanism 13 collapsed the medical device head (i.e. its proximal portion); and FIG. 18: the elongated tubular member 12 is pulled out in the proximal direction and the medical device 2 enters within the sheath 11.

FIGS. 19, 20 21 and 22 illustrate the deployment and recovery of a heart valve prosthesis in a atrioventricular native valve implantation site:

FIG. 19: a delivery apparatus according to one embodiment goes through the native valve. Due to its rigidity, the delivery apparatus is pushed against the native wall;

FIG. 20: the prosthesis is partially deployed and firmly retained by the retaining mechanism. The prosthesis is positioned at the correct location before full deployment;

FIG. 21: the retaining mechanism is disengaged and the heart valve prosthesis is left free to deploy at the desired level;

FIG. 22: if required, the heart valve prosthesis is removed through traction on holding and retrieving mechanism which pulled out and collapsed the prosthesis head.

FIG. 32a: the medical device 2 is in collapsed state, connected to retaining and holding and retrieving mechanisms of a delivery apparatus according to one embodiment.

FIG. 32b: the medical device 2 is partially deployed.

FIG. 32c: the retaining mechanism 13 is released.

FIG. 32d: the medical device 2 is freely and fully deployed. The medical device has a high degree of freedom relative to delivery system.

FIG. 32e: the medical device 2 is fully deployed. The holding and retaining mechanism is ready to be released.

FIG. 32f: the holding and retrieving mechanism 13 is released by pulling out the trigger wire 1233.

FIG. 32g: the delivery apparatus is pulled out and the holding and retrieving mechanism 13 is withdrawn from the medical device 2 proximal part.

FIG. 33a: the holding and retrieving mechanism 13 is a flexible wire. One looped end of the wire is connected to the elongated member 12 with a trigger wire. The other end of the retaining wire is free.

FIG. 33b: the free end of the retaining wire cross the filament and is connected to the elongated member 12 with fitting mean.

FIG. 38a illustrates the prosthesis head according to one embodiment with one interlaced filament to be used with the holding and retrieving mechanism.

FIG. 38b illustrates the prosthesis head with at least two interlaced filament to be used with the holding and retrieving mechanism.

FIGS. 39a and 39b illustrate the retaining mechanism according to another embodiment wherein the retaining mechanism has a rough surface.

FIG. 42a: the holding means is out of the sheath and releases the end of the holding and retrieving mechanism.

FIG. 42b: the holding means is in the sheath and hold the end of the holding and retrieving mechanism.

FIG. 44a: the pliers 1234 hold the holding and retrieving mechanism 13.

FIG. 44b: the holding and retrieving mechanism 13 is released.

REFERENCES

Figure 1:
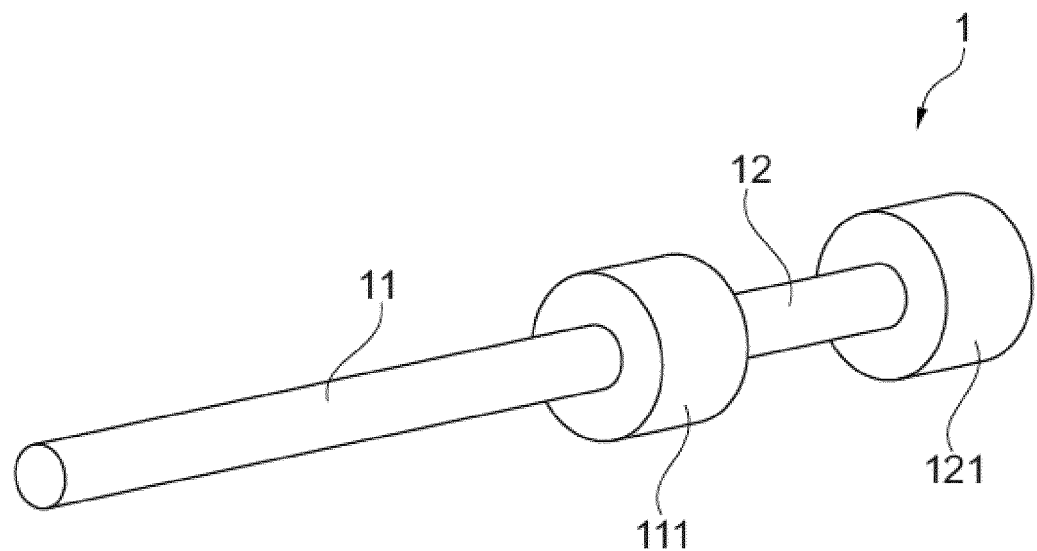
FIG. 1 is a schematic perspective view of a delivery apparatus 1 used to deliver and implant a medical device 2, such as a prosthetic heart valve.
Figure 2:
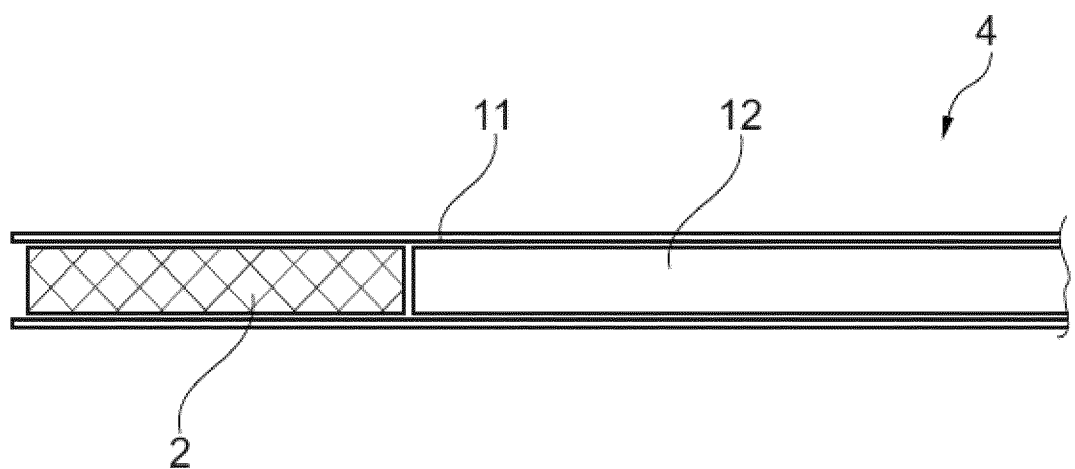
FIG. 2 is a schematic cross-sectional view of the distal portion of a delivery system 4 according to one embodiment with a loaded crimped medical device 2, such as a prosthetic heart valve.
Figure 3:
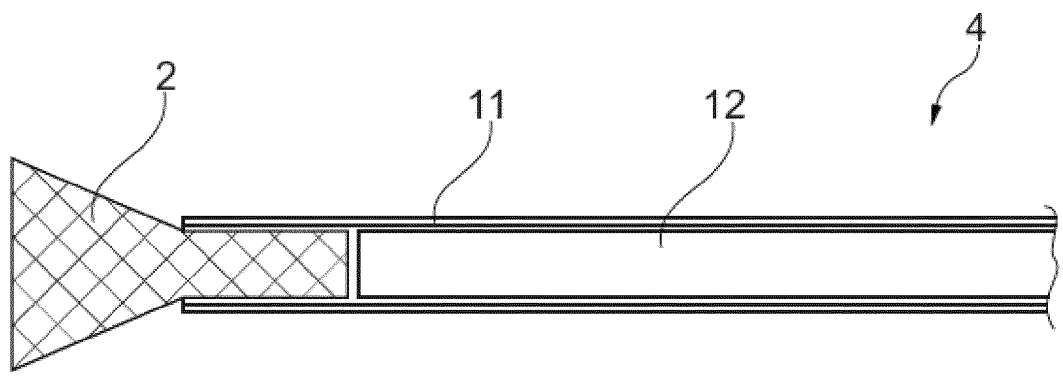
FIG. 3 is a schematic cross-sectional view of the distal portion of a delivery system 4 according to one embodiment with a partially deployed medical device 2, such as a prosthetic heart valve.
Figure 4:
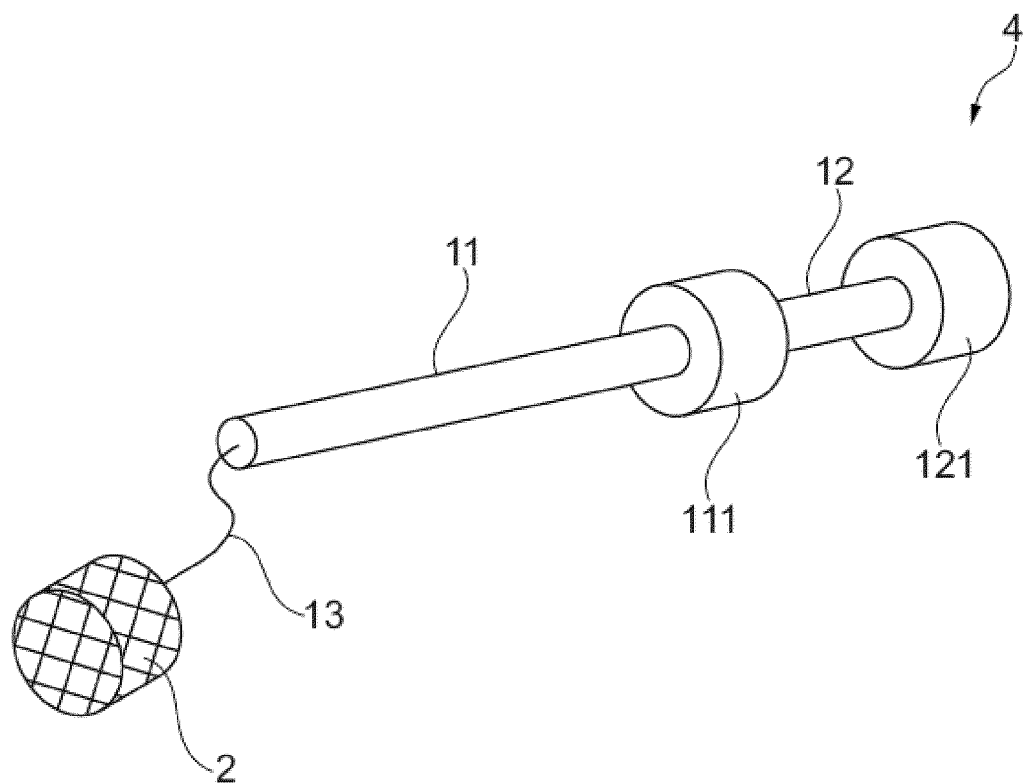
FIG. 4 is a schematic perspective view of a delivery system 4 according to one embodiment after complete deployment of a medical device 2, such as a prosthetic heart valve.
Figure 5:
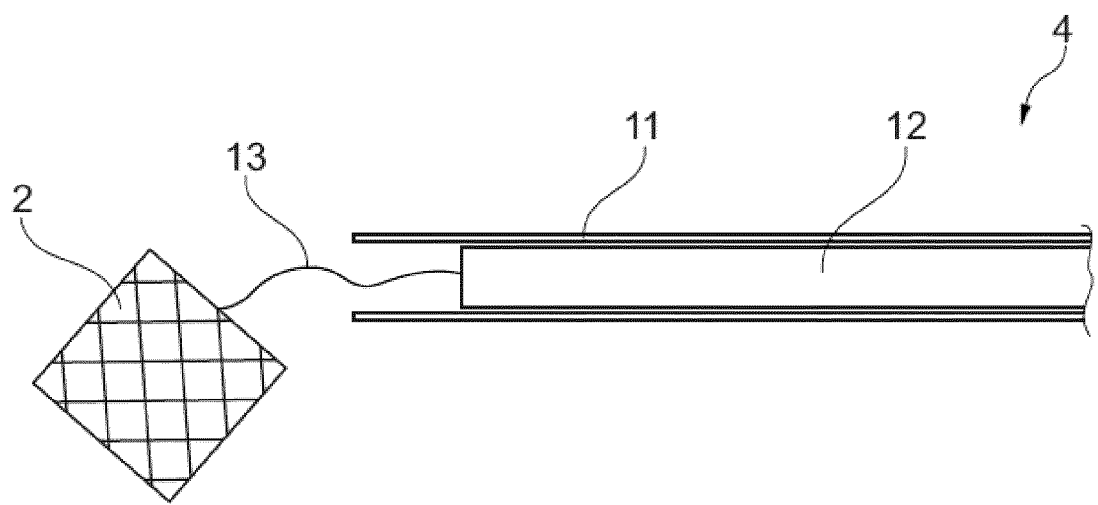
FIG. 5 is a schematic cross-sectional view of the distal portion of a delivery system 4 according to one embodiment after complete deployment of a medical device 2, such as a prosthetic heart valve.
Figure 6:
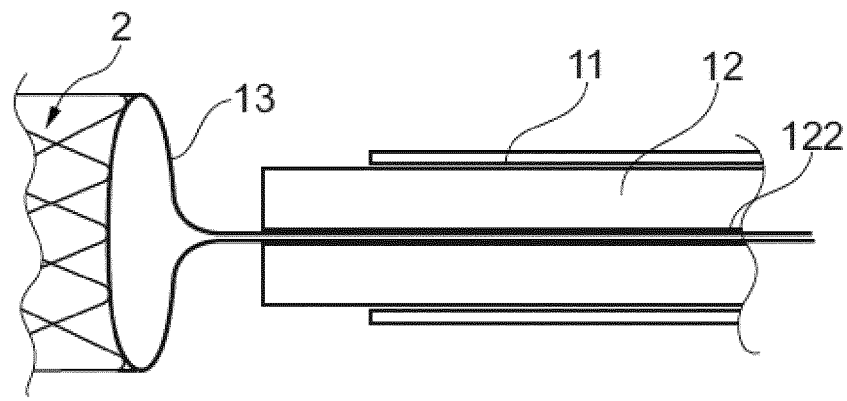
FIG. 6 is a schematic cross-sectional view of the distal portion of a delivery system 4 with a holding and retrieving mechanisms 13 passing through the whole length of the lumen 122 of the elongated tubular member 12.
Figure 7:
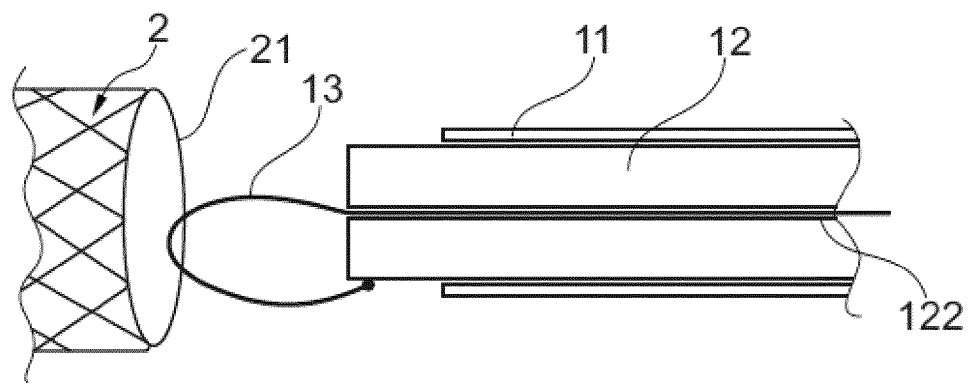
FIG. 7 is a schematic cross-sectional view of the distal portion of a delivery system 4 with a holding and retrieving mechanisms 13 passing through the whole length of the lumen 122 of the elongated tubular member 12.
Figure 8:
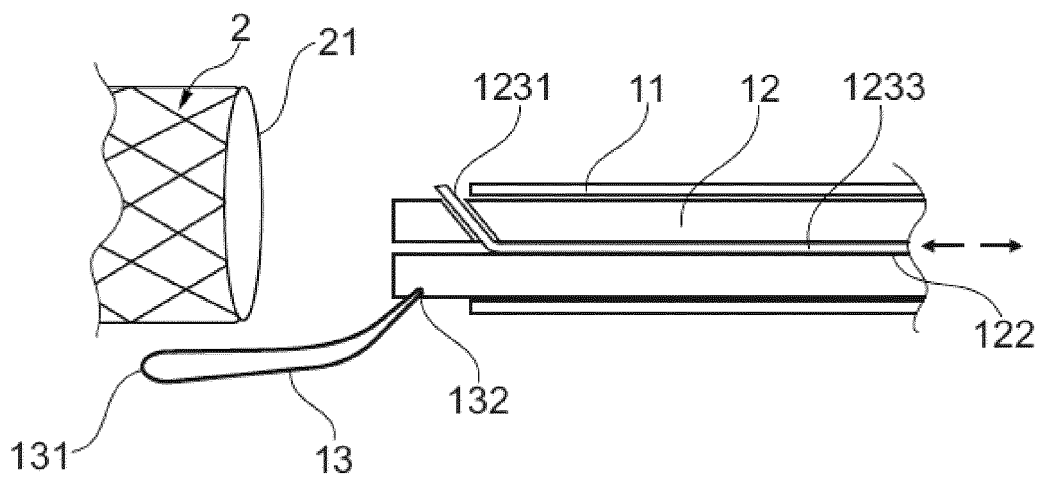
FIGS. 8 and 9 are schematic cross-sectional views of the distal portion of a delivery system 4 according to one embodiment, illustrating the first holding means of the holding and retrieving mechanism 13.
Figure 9:
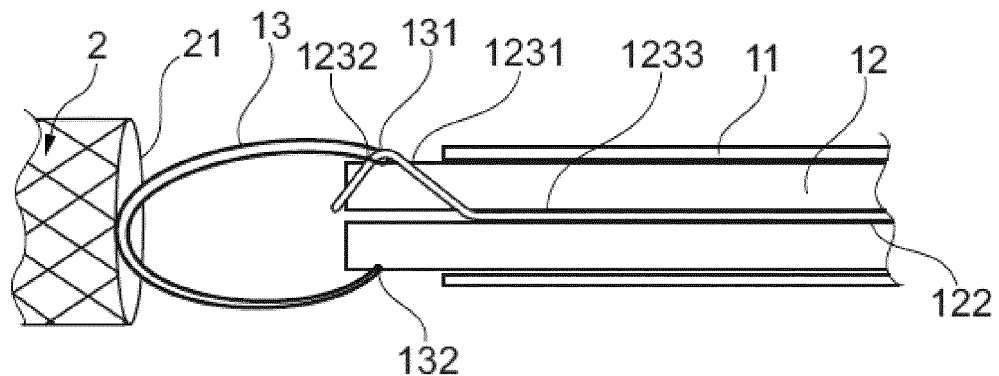
Figure 10:
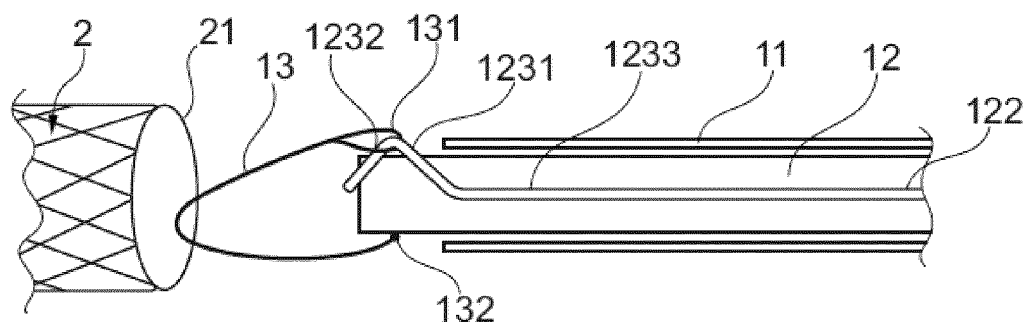
FIG. 10 is schematic cross-sectional view of the distal portion of a delivery system 4 according to one embodiment, illustrating a holding and retrieving mechanism 13 comprising a closed loop at one end.
Figure 11:
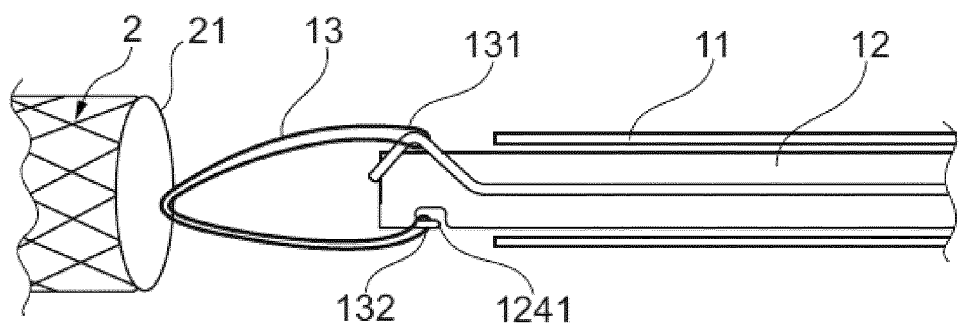
FIG. 11 is schematic cross-sectional view of the distal portion of a delivery system 4 according to one embodiment, illustrating the second holding means of a holding and retrieving mechanism 13 wherein the elongated tubular member 12 comprises a hook 1241 and wherein the second end of the holding and retrieving mechanism 132 comprises a loop configured to be hooked to the said hook 1241.
Figure 12:
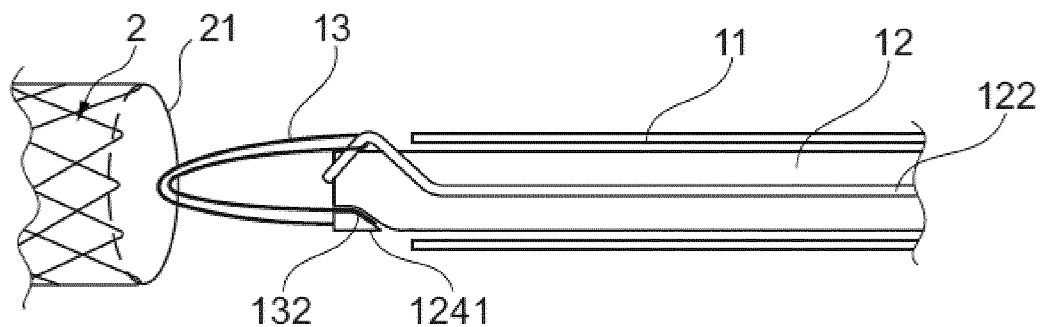
FIG. 12 is schematic cross-sectional view of the distal portion of a delivery system 4 according to one embodiment, illustrating the second holding means of a holding and retrieving mechanism 13 wherein the elongated tubular member 12 comprises a recessed hook 1241 and wherein the second end of the holding and retrieving mechanism 132 comprises a distal part having a shape complementary to the shape of the recessed hook 1241.
Figure 13:
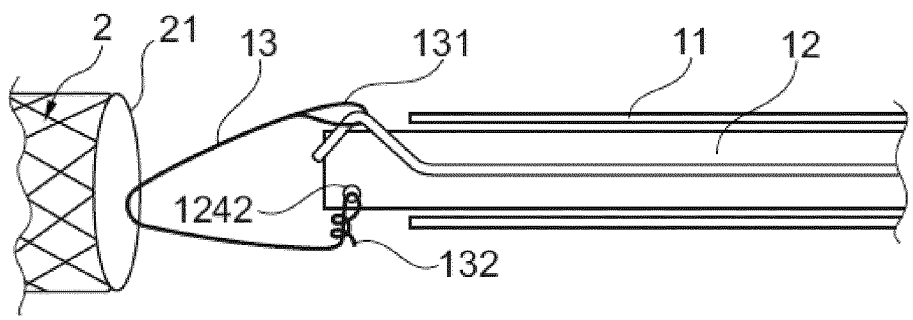
FIG. 13 is schematic cross-sectional view of the distal portion of a delivery system 4 according to one embodiment, illustrating the second holding means of a holding and retrieving mechanism 13 wherein the elongated tubular member 12 comprises a through-hole 1242 from the outer wall to the outer wall and wherein the second end of the holding and retrieving mechanism 132 may be knotted to the elongated tubular member 12 through said trough-hole 1242.
Figure 14:
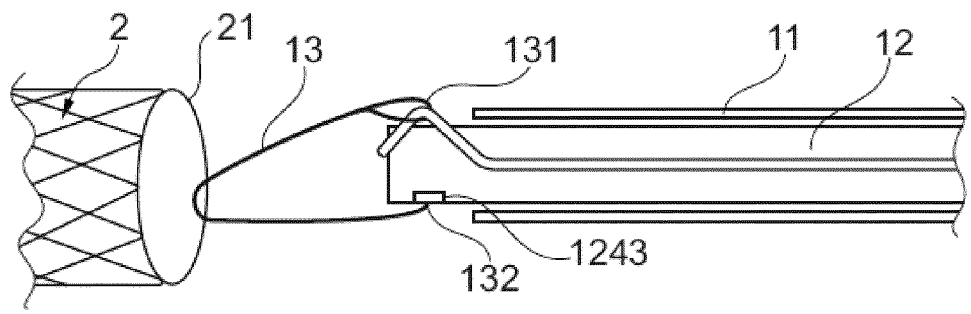
FIG. 14 is schematic cross-sectional view of the distal portion of a delivery system 4 according to one embodiment, illustrating the second holding means of a holding and retrieving mechanism 13 wherein an end 132 of the holding and retrieving mechanism has a shape that fit closely with a recess 1243 located on the distal portion of the elongated tubular member 12.
Figure 15:
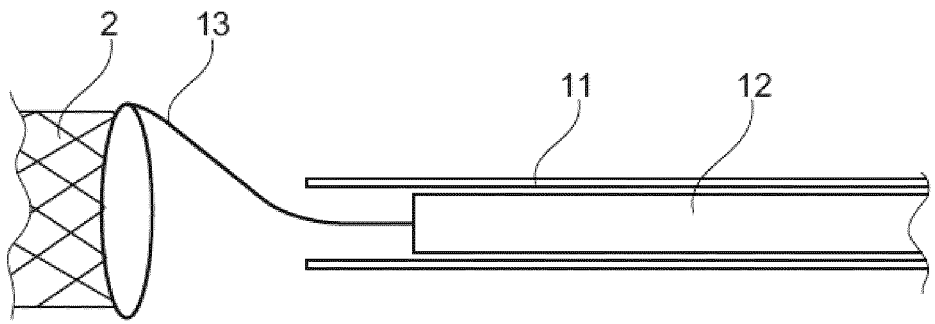
FIGS. 15, 16, 17 and 18 illustrate step by step views the medical device 2, such as a prosthetic heart valve, retrieval from a fully deployed state.
Figure 16:
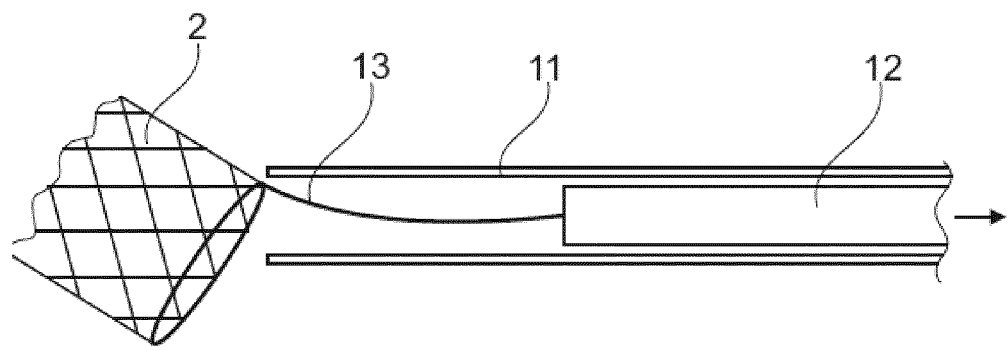
Figure 17:
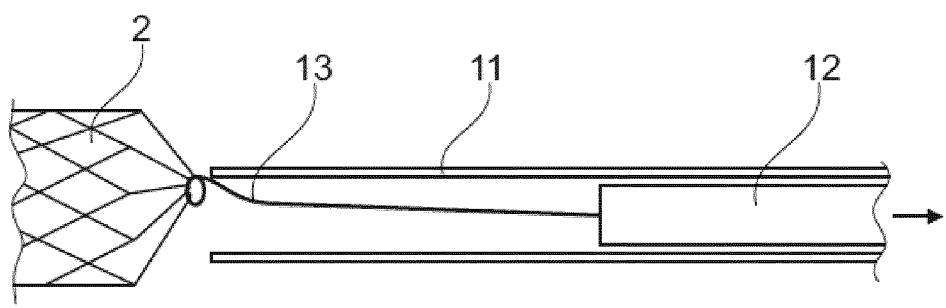
Figure 18:
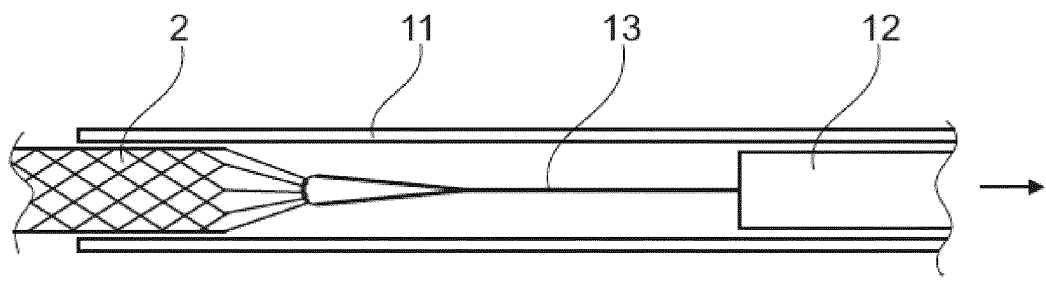
Figure 23:
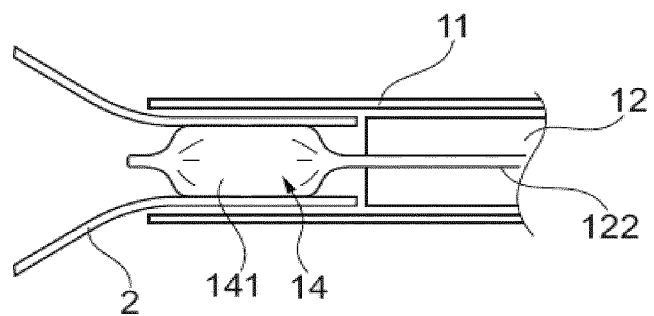
FIGS. 23 and 24 are schematic cross-sectional views of the distal portion of a delivery system 4 according to one embodiment with a partially deployed medical device 2, such as a prosthetic heart valve, wherein a balloon located within the head of a partially deployed medical device is used as a retaining mechanism. The balloon is reversibly expandable from a collapsed profile (FIG. 24) to an expanded profile (FIG. 23).
Figure 24:
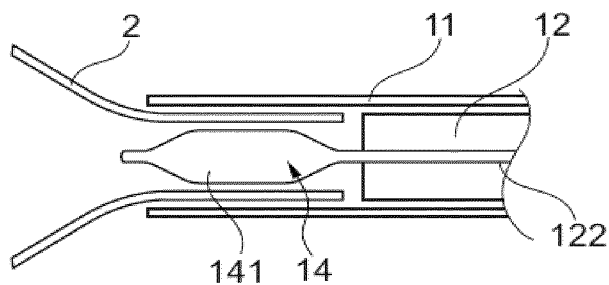
Figure 25:
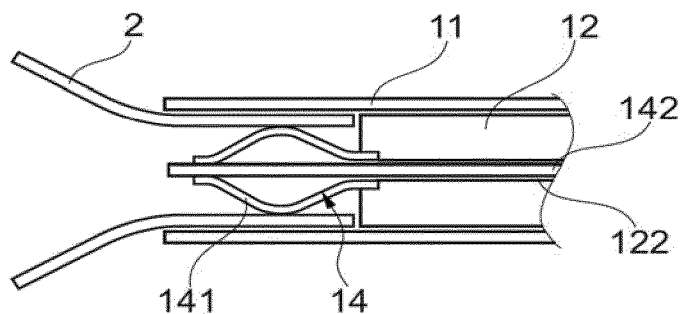
FIGS. 25 and 26 are schematic cross-sectional views of the distal portion of a delivery system 4 according to one embodiment with a partially deployed medical device 2, such as a prosthetic heart valve, wherein a retaining mechanism according to one embodiment is engaged within the head of a partially deployed medical device. The retaining mechanism is reversibly expandable from a collapsed profile (FIG. 26) to an expanded profile (FIG. 25).
Figure 26:
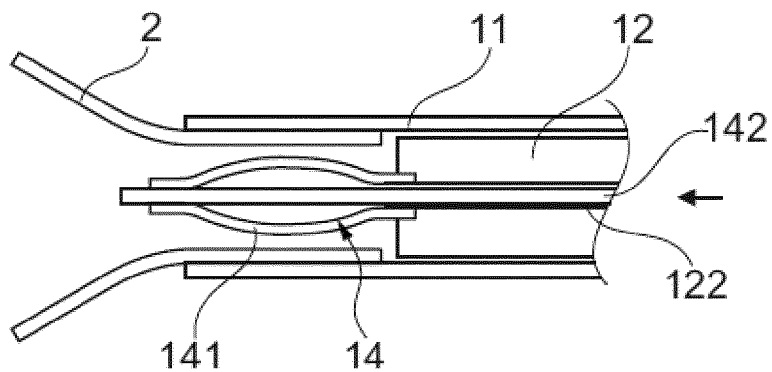
Figure 27:
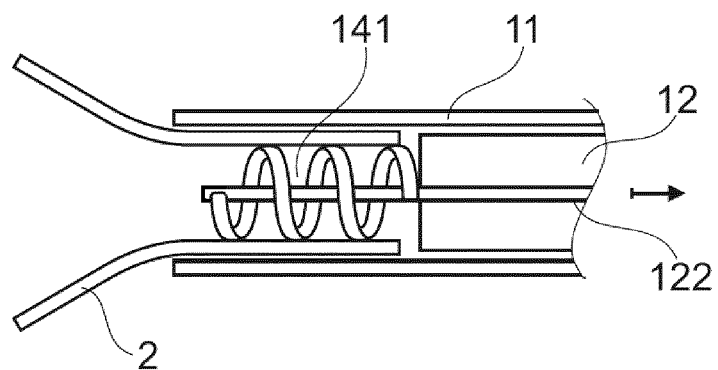
FIGS. 27 and 28 are schematic cross-sectional views of the distal portion of a delivery system 4 according to one embodiment with a partially deployed medical device 2, such as a prosthetic heart valve, wherein a retaining mechanism according to one embodiment is engaged within the head of a partially deployed medical device. The retaining mechanism is reversibly expandable from a collapsed profile (FIG. 28) to an expanded profile (FIG. 27).
Figure 28:
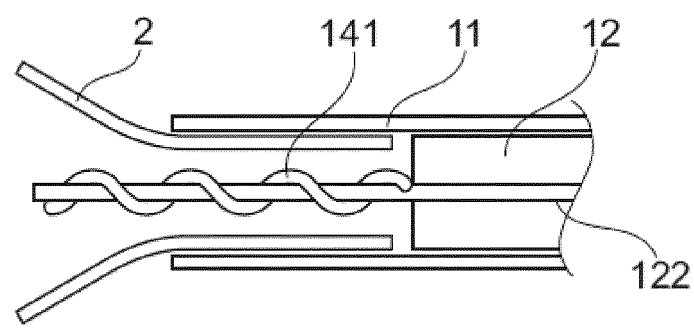
Figure 29:
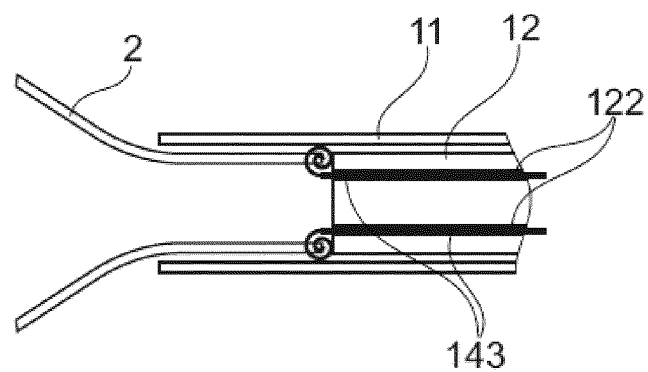
FIGS. 29 and 30 are schematic cross-sectional views of the distal portion of a delivery system 4 according to one embodiment with a partially deployed medical device 2, such as a prosthetic heart valve, wherein coiled tethers embedded within the head of a partially deployed medical device are used as retaining mechanism.
Figure 30:
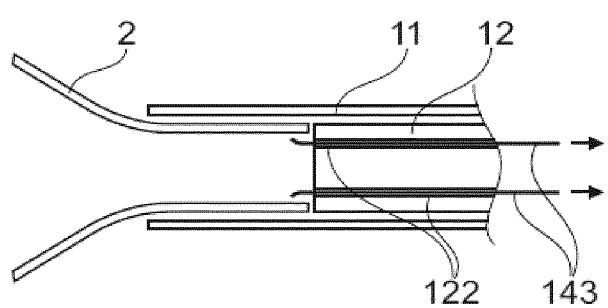
Figure 31:
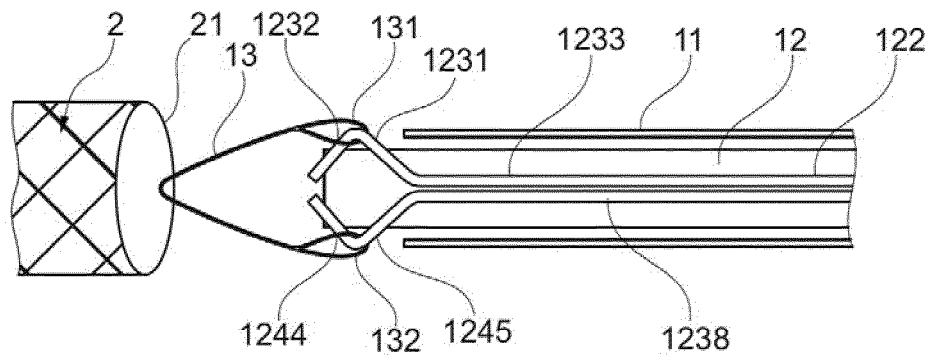
FIG. 31 is schematic cross-sectional view of the distal portion of a delivery system 4 according to one embodiment, illustrating the second holding means of a holding and retrieving mechanism 13 wherein the elongated tubular member 12 comprises a third and a fourth apertures through the elongated tubular member from the lumen to an outer wall.
Figure 32A:
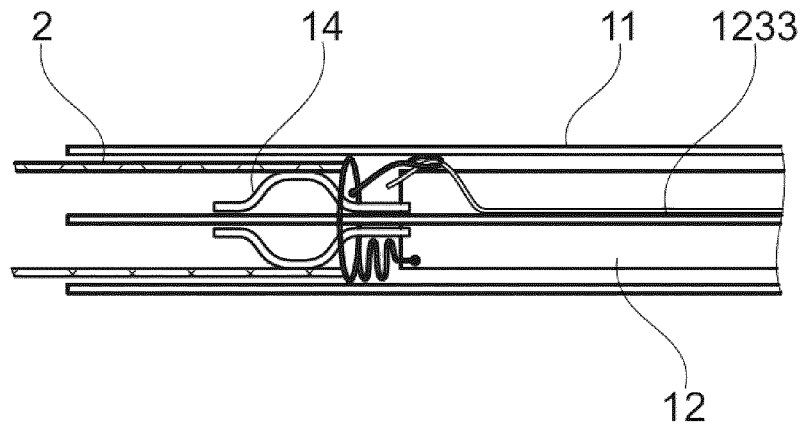
FIGS. 32a to 32g illustrate step by step the medical device 2 deployment and implantation.
Figure 32B:
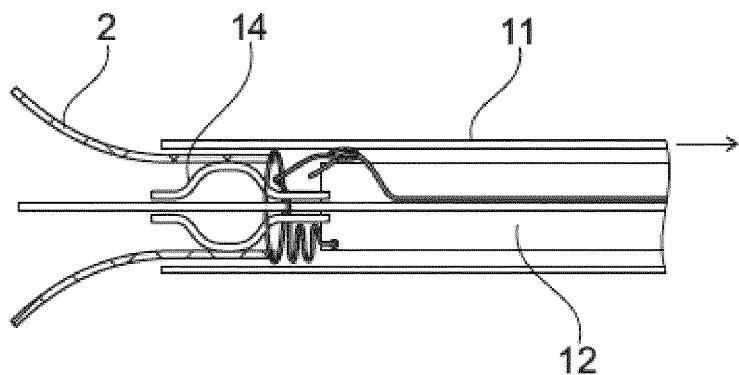
Figure 32C:
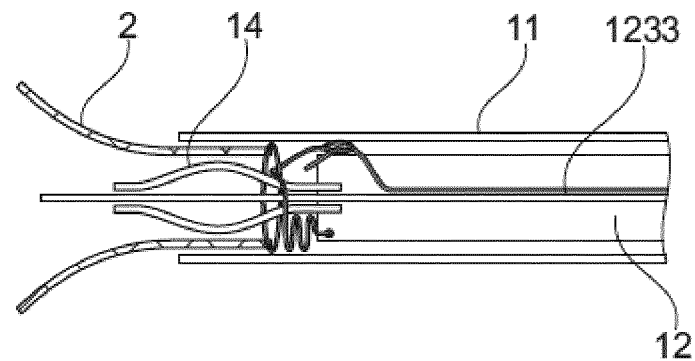
Figure 32D:
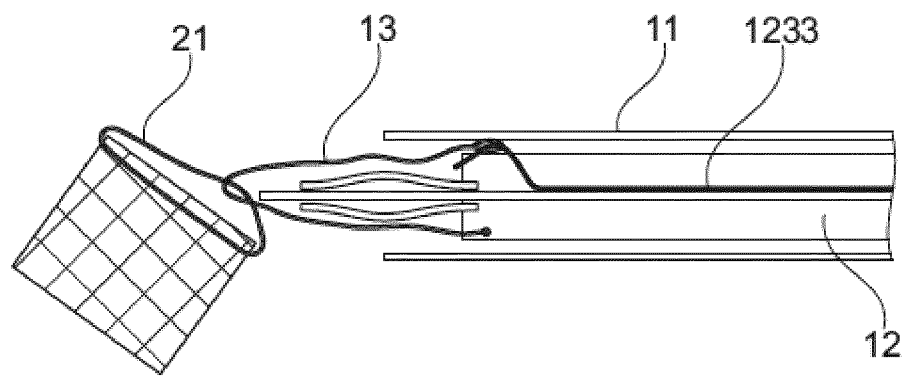
Figure 32E:
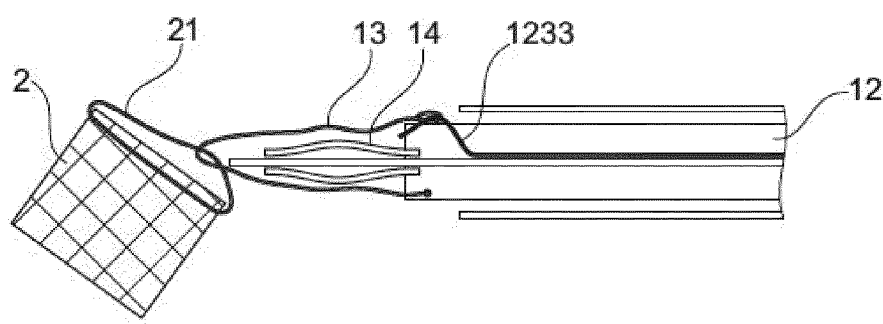
Figure 32F:
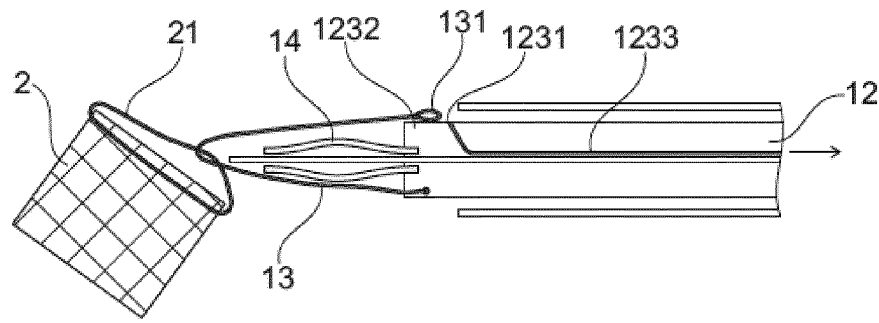
Figure 32G:
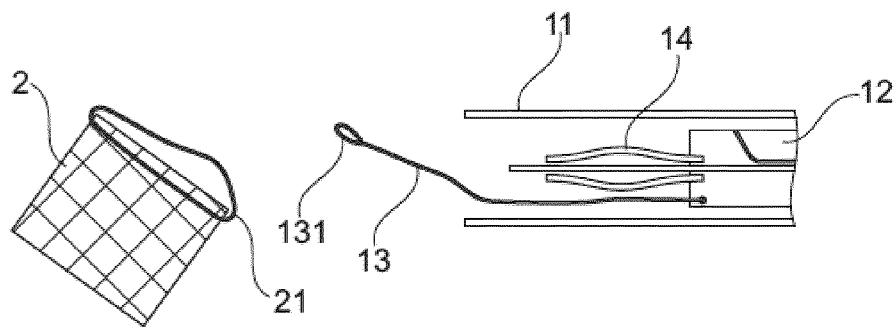
Figure 33A:
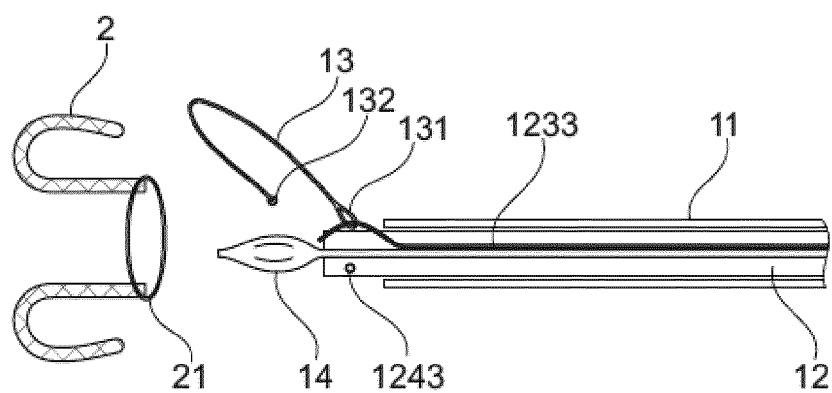
FIGS. 33a, 33b illustrate double wall medical device according to one embodiment being connected to the holding and retrieving mechanism of the delivery apparatus according to one embodiment.
Figure 33B:
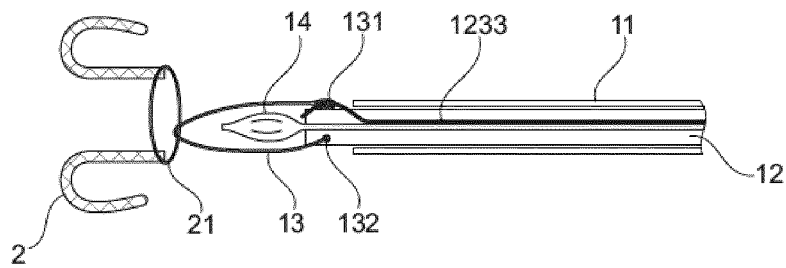
Figure 34A:
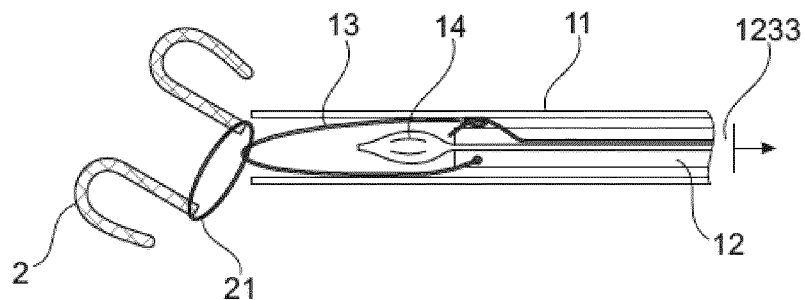
FIGS. 34a and 34b: the elongated member is pulled out in proximal direction until medical device inner part is collapsed within the sheath.
Figure 34B:
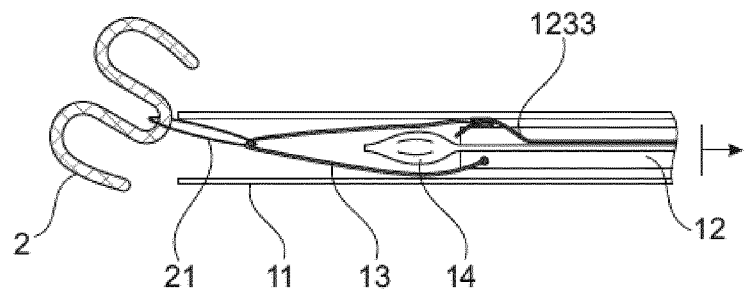
Figure 35A:
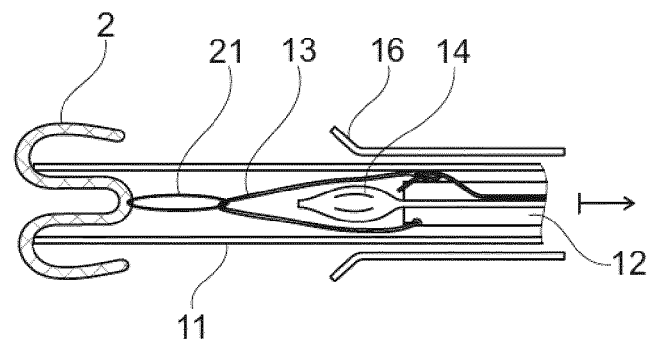
FIGS. 35a and 35b: an external coaxial and slightly larger sheath help to collapse the outer wall of the prosthesis in a double wall crimped configuration. Preferably, the external sheath has a flared distal end.
Figure 35B:
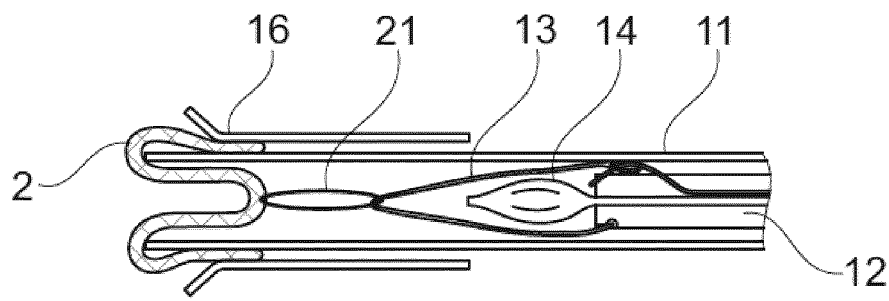
Figure 36A:
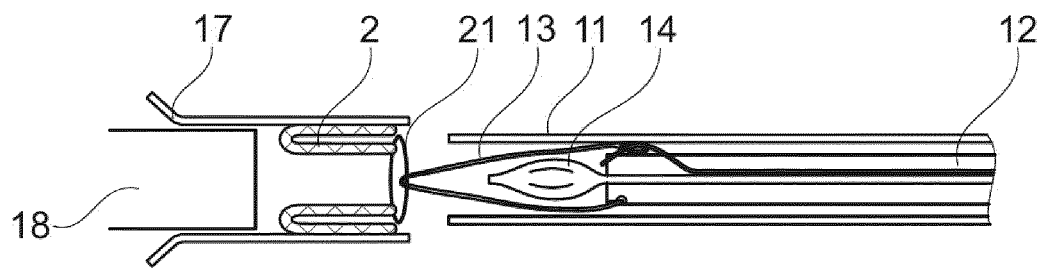
FIGS. 36a and 36b: the collapsed prosthesis is transfer into the catheter sheath. The retaining mechanism is placed within the prosthesis.
Figure 36B:
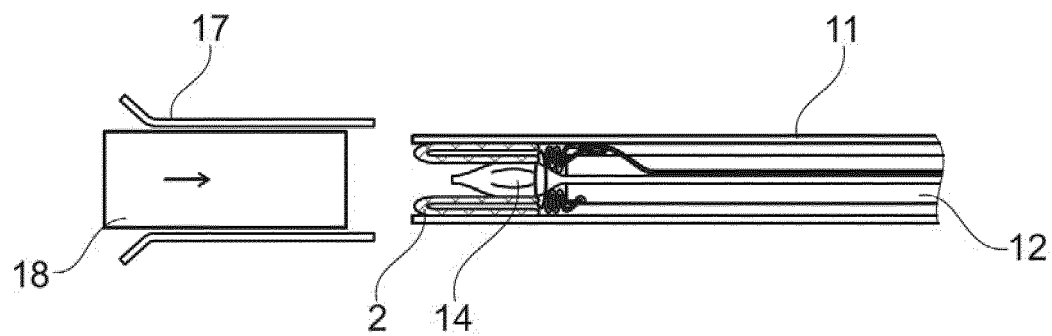
Figure 36C:
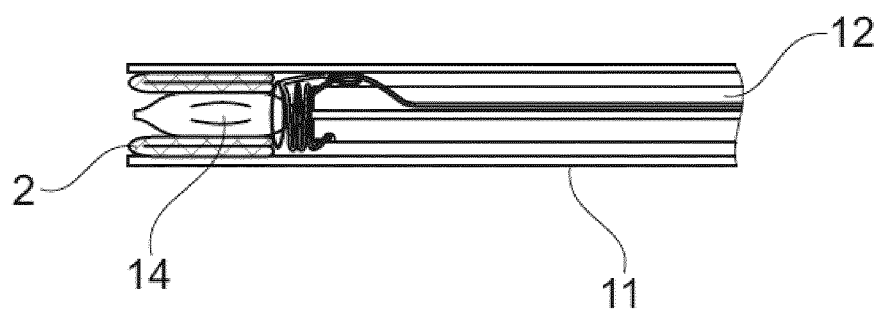
FIG. 36c: the retaining mechanism 14, a balloon, is activated.
Figure 37A:
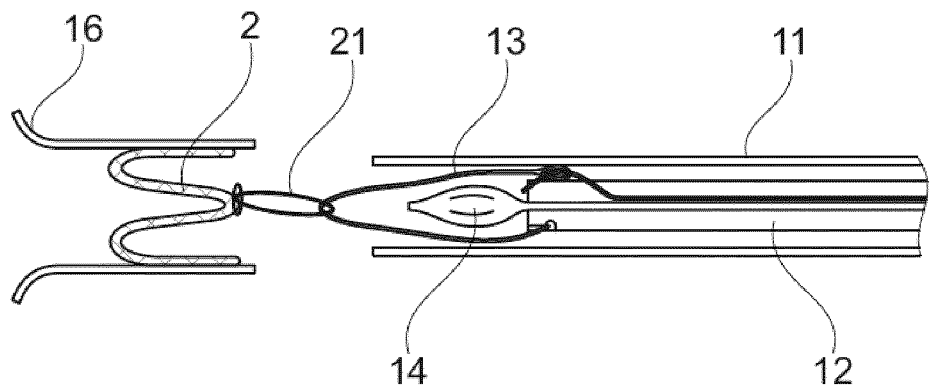
FIGS. 37a, 37b, 37c illustrate double-wall prosthesis according to one embodiment crimped in an additional sheath with at least 2 filaments at the head of the prosthesis. The first filament is used to crimp the prosthesis and is removed from the prosthesis before loading in the catheter. The second filament is used to connect the prosthesis to the elongated member with holding and retrieving mechanism.
Figure 37B:
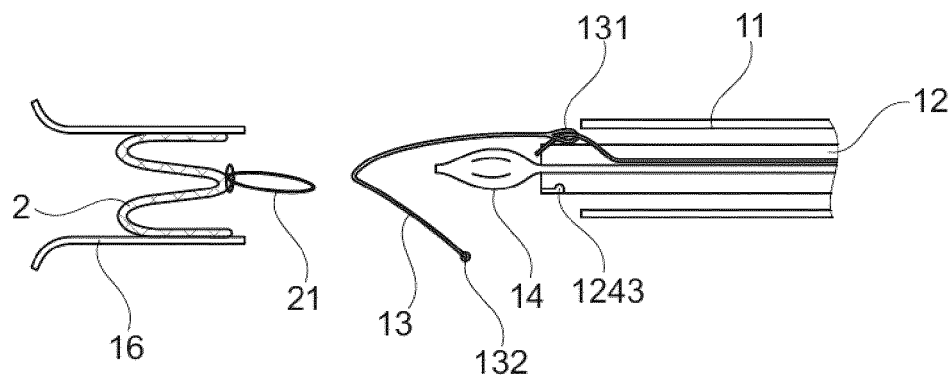
Figure 37C:
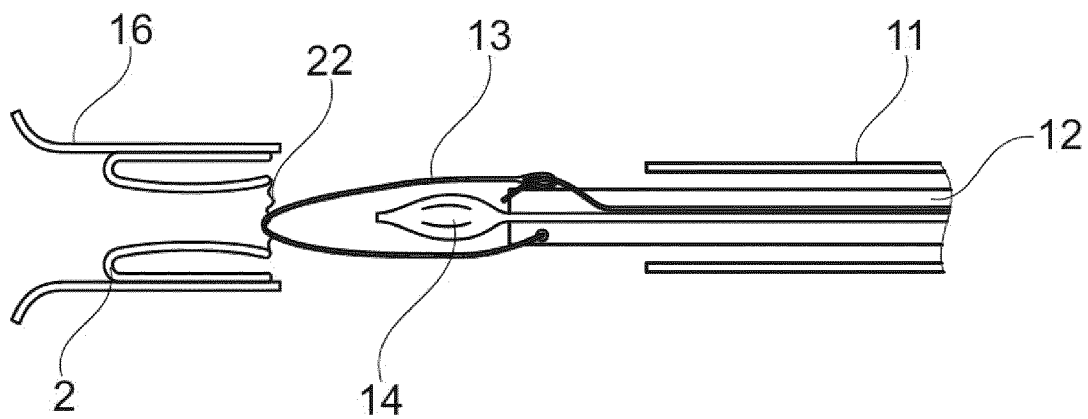
Figure 40A:
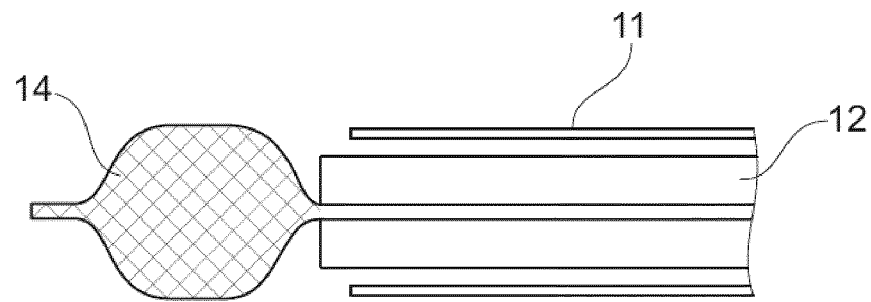
FIGS. 40a and 40b illustrate the retaining mechanism according to another embodiment wherein the retaining mechanism has an elastic and compressible component.
Figure 40B:
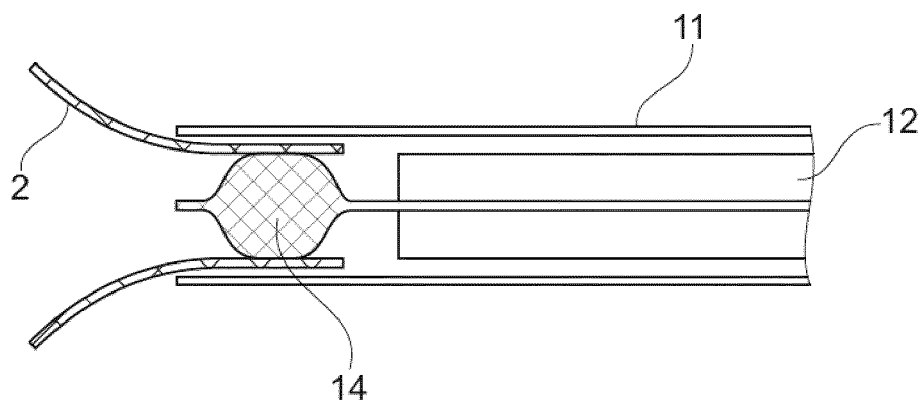
Figures 41A, 41B, 41C:
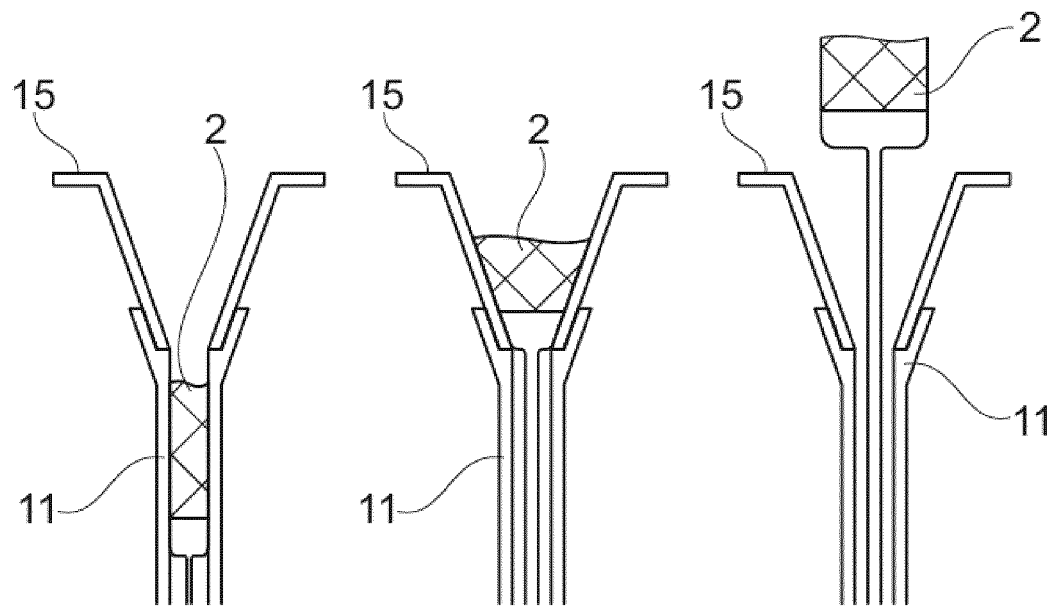
FIGS. 41a, 41b, 41c illustrate the delivery system comprises a cone at its distal part.
Figure 42A:
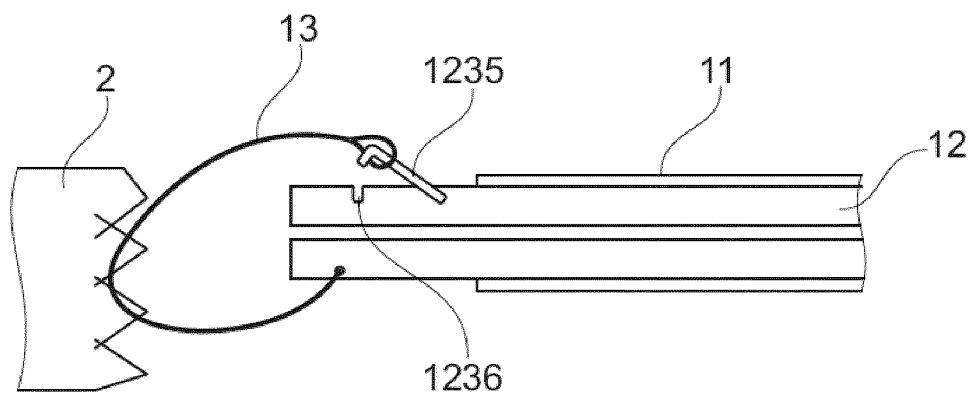
FIGS. 42a and 42b illustrate the first holding means according to one embodiment wherein the first holding means is an elastic hook which catch the second end of the holding and retrieving mechanism in an aperture 1236.
Figure 42B:
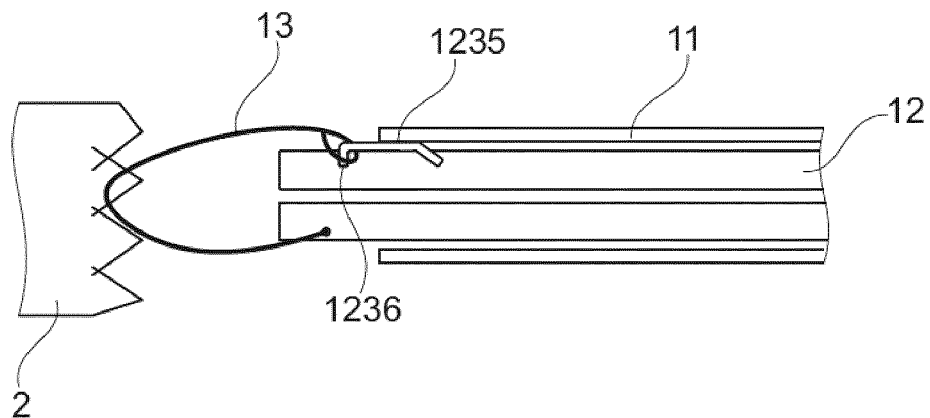
Figure 43A:
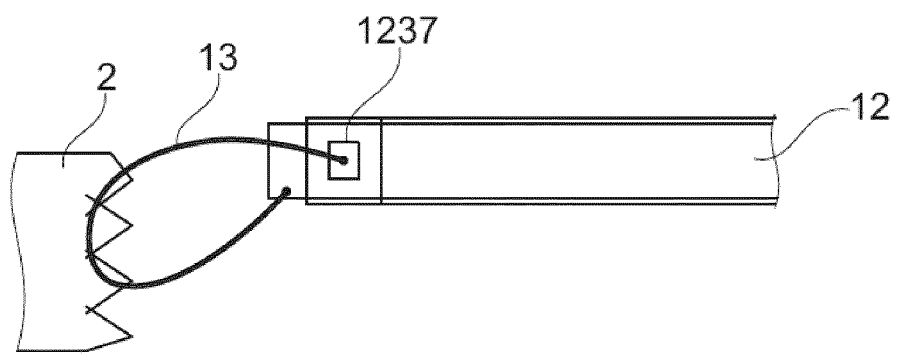
FIGS. 43a and 43b illustrate the elongated member according to one embodiment. This elongated member comprises a coaxial element which comprises a sharp window. One end of the holding and retrieving mechanism is secured to the elongated member and passes through the sharp window. The relative movement of the coaxial element regarding the elongated member cut the holding and retrieving mechanism (FIG. 43b). The sheath is not illustrated on this figure.
Figure 43B:
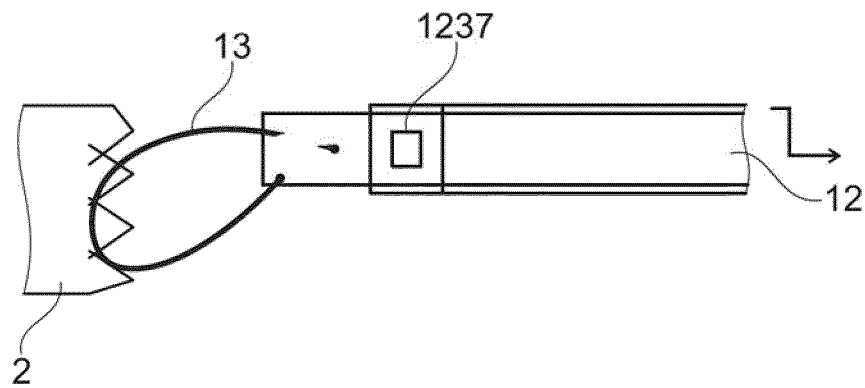
Figure 44A:
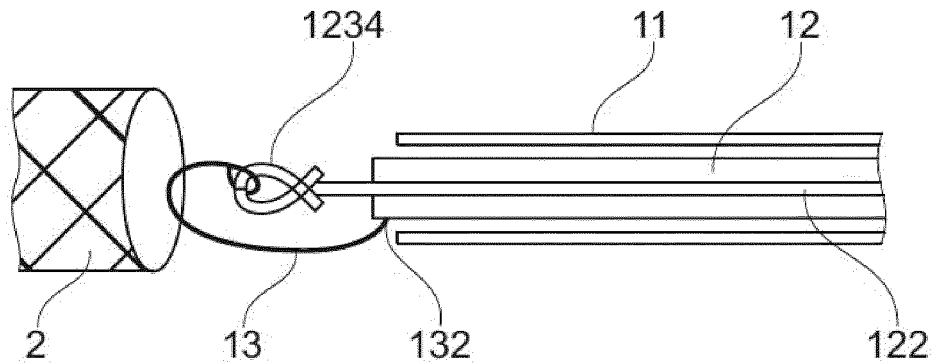
FIGS. 44a and 44b illustrate the first holding means according to one embodiment. The holding means are retrieving pliers 1234.
Figure 44B:
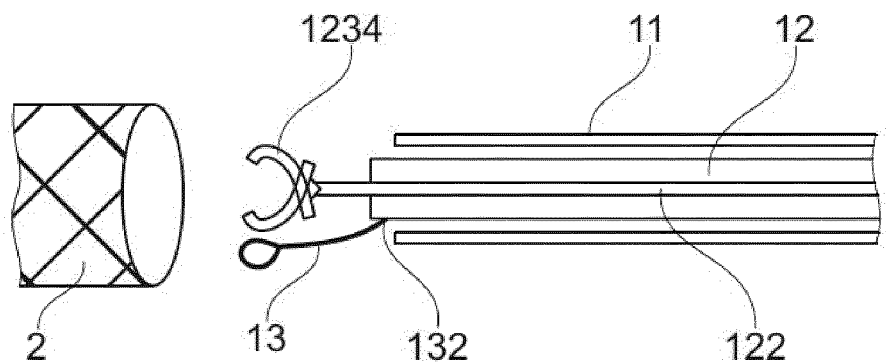
Figure 45:
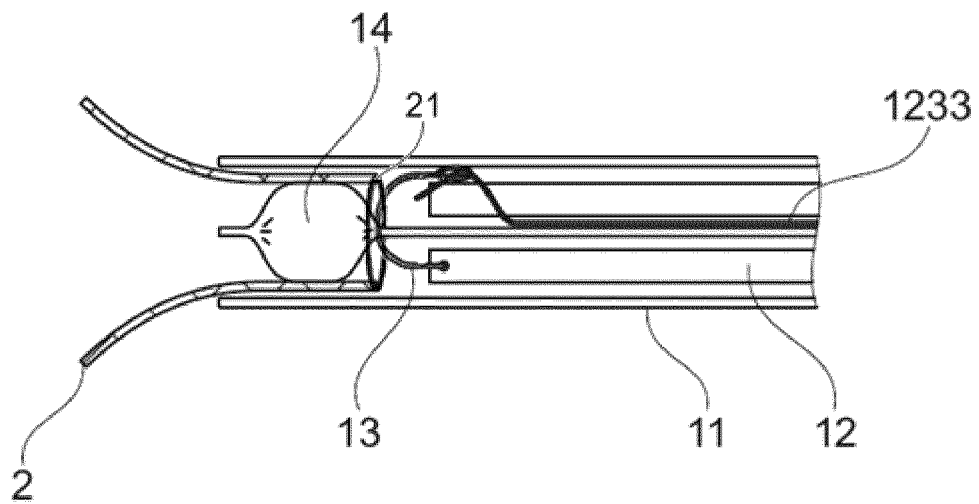
FIG. 45 illustrates the delivery system according to one embodiment wherein the elongated member is not in contact with the medical device. In said embodiment, the elongated member is not used for pushing the medical device outside the sheath.
Figure 46A:
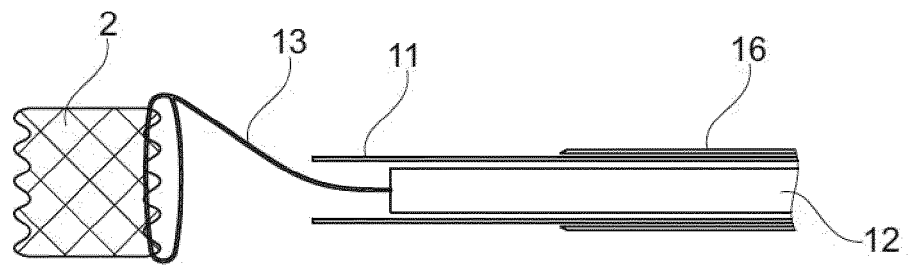
FIGS. 46a, 46b, 46c, 46d, 46e, illustrate the medical device 2 retrieval from a fully deployed state with help of an additional coaxial and slightly larger sheath 16.
Figure 46B:
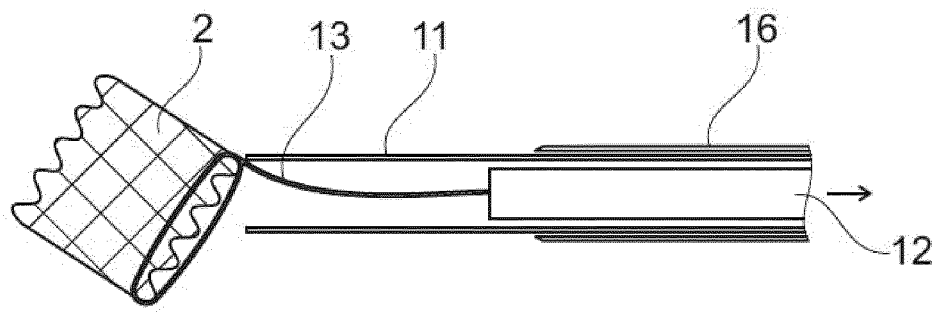
Figure 46C:
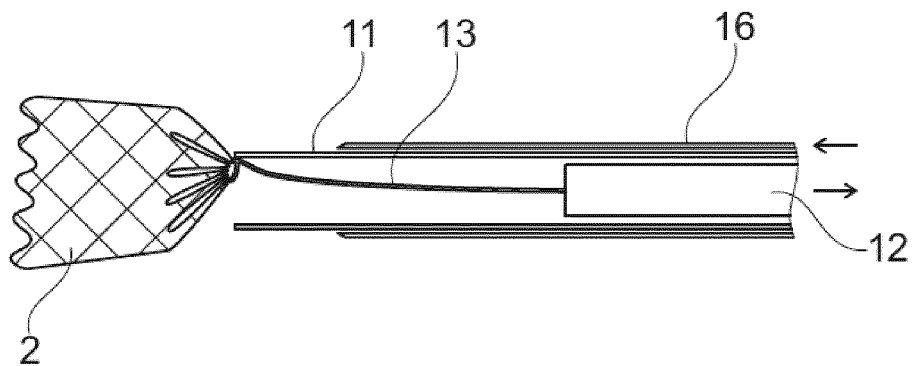
Figure 46D:
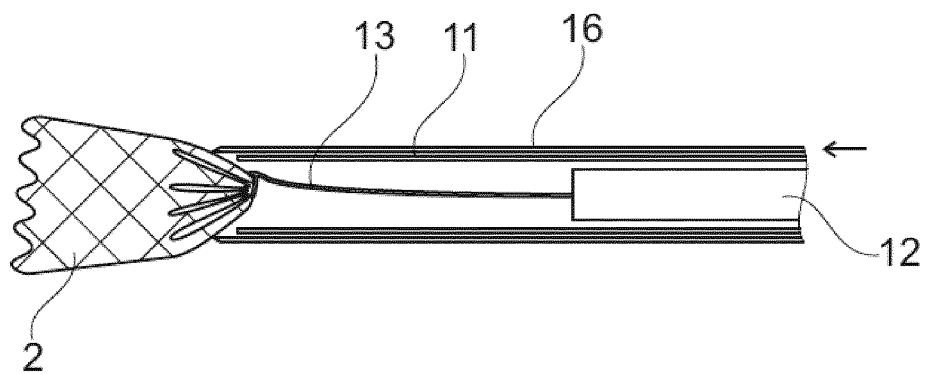
Figure 46E:
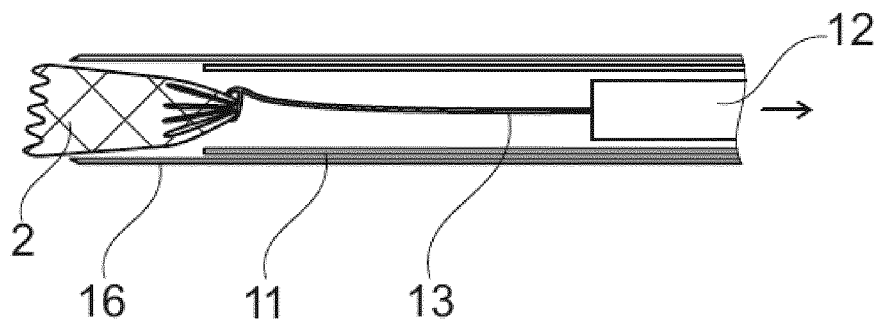

1—Delivery apparatus
11—Sheath
111—Handle
12—Elongated tubular member
121—Handle
122—Lumen
1231—First aperture of the first holding means
1232—Second aperture of the first holding means
1233—Trigger wire of the first holding means
1234—Retrieving hook
1235—Elastic holding means
1236—Aperture of the first holding means
1237—Sharp window
1238—Trigger wire of the second holding means
1241—Hook of the second holding means
1242—Through-hole of the second holding means
1243—Recess of the second holding means
1244—Fourth aperture of the second holding means
1245—Third aperture of the second holding means
13—Holding and retrieving mechanism
131—First end
132—Second end
14—Retaining mechanism
141—Expandable portion
142—Actuator
143—Wire
15—Cone
16—External sheath
17—Tubular support
18—Transferring means
2—Radially self-expanding medical device
21—Filament
22—Second Filament
3—Heart
4—Delivery system

What is claimed is:

1. A delivery apparatus for delivering a radially self-expanding medical device having a proximal portion and a distal portion, said delivery apparatus comprising:
   i. a radially self-expanding medical device having a proximal end and a distal end;
   ii. an elongated tubular member having a proximal end, a distal end, and a lumen extending along a longitudinal axis from the proximal end to the distal end;
   iii. a sheath, said sheath being coaxially disposed around the elongated tubular member; wherein the elongated tubular member is movable relative to the sheath; and wherein the sheath is configured for receiving the radially self-expanding medical device in a radially compressed state; and
   iv. a holding and retrieving mechanism having a first end and a second end; the holding and retrieving mechanism being configured to constrain radially the proximal portion of the radially self-expanding medical device such that in response to a proximal movement of the elongated tubular member relative to the sheath, the holding and retrieving mechanism constrains radially the proximal portion of the radially self-expanding medical device and the radially self-expanding medical device is collapsed within the sheath;
   wherein the elongated tubular member is capable of releasably holding the first and second ends of the holding and retrieving mechanism near the distal end of the elongated tubular member and releasing the first end with an actuation at the proximal end of the elongated tubular member; and
   wherein the holding and retrieving mechanism is connected only to the proximal end of the radially self-expanding medical device;
   wherein the releasable holding of the first end of the holding and retrieving mechanism is achieved by a first aperture and a second aperture through the elongated tubular member from the lumen to an outer wall, said first and second apertures being disposed near the distal end of the elongated tubular member and said first aperture being disposed proximally of said second aperture; and a trigger wire disposed within the lumen of the elongated tubular member; the trigger wire exits said lumen of said elongated tubular member through the first aperture and re-enters said lumen of said elongated tubular member through the second aperture such that said trigger wire forms a bend, said bend of said trigger wire engaging said first end of the holding and retrieving mechanism; said trigger wire being configured to be withdrawn in the proximal direction through said lumen of said elongated tubular member such that said trigger wire disengages said first end of the holding and retrieving mechanism.

2. The delivery apparatus of claim 1, wherein the holding and retrieving mechanism comprises a longitudinal axis and the ratio between the length along the longitudinal axis and the greater length in the transverse plane is greater than 3.

3. The delivery apparatus of claim 1, wherein the releasable holding of the second end of the holding and retrieving mechanism is achieved with a third aperture and a fourth aperture through the elongated tubular member from the lumen to an outer wall, said third and fourth aperture being disposed near the distal end of the elongated tubular member and said third aperture being disposed proximally of said fourth aperture; and a trigger wire disposed within the lumen of the elongated tubular member; the trigger wire exits said lumen of said elongated tubular member through the third aperture and re-enters said lumen of said elongated tubular member through the fourth aperture such that said trigger wire forms a bend, said bend of said trigger wire engaging said second end of the holding and retrieving mechanism; said trigger wire being configured to be withdrawn in the proximal direction through said lumen of said elongated tubular member such that said trigger wire disengage said second end of the holding and retrieving mechanism.

4. The delivery apparatus of claim 1, wherein the elongated tubular member non-detachably holds the second end of the holding and retrieving mechanism near the distal end of the elongated tubular member with a hook and the second end of the holding and retrieving mechanism comprises a loop configured to be hooked to the hook of the elongated tubular member.

5. The delivery apparatus of claim 1, wherein the elongated tubular member non-detachably holds the second end of the holding and retrieving mechanism near the distal end of the elongated tubular member with a through-hole in the elongated tubular member and wherein the second end of the holding and retrieving mechanism may be knotted to the elongated tubular member through said trough-hole.

6. The delivery apparatus of claim 1, wherein the elongated tubular member non-detachably holds the second end of the holding and retrieving mechanism near the distal end of the elongated tubular member by a recess having a shape complementary to the shape of the distal end of the holding and retrieving mechanism, said recess being configured for retaining the distal end of the holding and retrieving mechanism.

7. The delivery apparatus of claim 1, wherein the radially self-expanding medical device comprises a plurality of proximal apices disposed at a proximal end of the radially self-expanding medical device; and wherein the holding and retrieving mechanism engages at least one apex.

8. The delivery apparatus of claim 1, wherein the radially self-expanding medical device comprises a plurality of proximal apices disposed at a proximal end of the radially self-expanding medical device and a filament extending through the plurality of proximal apices; and wherein the holding and retrieving mechanism engages the filament.

9. The delivery apparatus of claim 1, wherein the radially self-expanding medical device comprises a radially collapsible and expandable heart valve prosthesis.

10. A delivery apparatus for delivering a radially self-expanding medical device having a proximal portion and a distal portion, said delivery apparatus comprising:
  i. a radially self-expanding medical device having a proximal end and a distal end;
  ii. an elongated tubular member having a proximal end, a distal end, and a lumen extending along a longitudinal axis from the proximal end to the distal end;
  iii. a sheath, said sheath being coaxially disposed around the elongated tubular member; wherein the elongated tubular member is movable relative to the sheath; and
  wherein the sheath is configured for receiving the radially self-expanding medical device in a radially compressed state; and
  iv. a holding and retrieving mechanism having a first end and a second end; the holding and retrieving mechanism being configured to constrain radially the proximal portion of the radially self-expanding medical device such that in response to a proximal movement of the elongated tubular member relative to the sheath, the holding and retrieving mechanism constrains radially the proximal portion of the radially self-expanding medical device and the radially self-expanding medical device is collapsed within the sheath;
  wherein the elongated tubular member is capable of releasably holding the first and second ends of the holding and retrieving mechanism near the distal end of the elongated tubular member and releasing the first end by an actuation at the proximal end of the elongated tubular member; and wherein the holding and retrieving mechanism is connected only to the proximal end of the radially self-expanding medical device;
  wherein the delivery apparatus includes a retaining mechanism configured for releasably retaining the radially self-expanding medical device within the sheath; said retaining mechanism comprising a first portion connected to the elongated tubular member and a second expandable portion disposed adjacent the distal end of the elongated tubular member and extending through the proximal portion of the radially self-expanding medical device, said second expandable portion being configured to expand from a collapsed profile to an expanded profile wherein the second expandable portion presses the proximal portion of the radially self-expanding medical device against the inner wall of the sheath so as to secured the radially self-expanding medical device therein; and wherein the second expandable portion exhibits a longitudinal flexibility.

11. The delivery apparatus of claim 10, wherein the releasable holding of the first end of the holding and retrieving mechanism is achieved with a first aperture and a second aperture through the elongated tubular member from the lumen to an outer wall, said first and second apertures being disposed near the distal end of the elongated tubular member and said first aperture being disposed proximally of said second aperture; and a trigger wire disposed within the lumen of the elongated tubular member; the trigger wire exits said lumen of said elongated tubular member through the first aperture and re-enters said lumen of said elongated tubular member through the second aperture such that said trigger wire forms a bend, said bend of said trigger wire engaging said first end of the holding and retrieving mechanism; said trigger wire being configured to be withdrawn in the proximal direction through said lumen of said elongated tubular member such that said trigger wire disengages said first end of the holding and retrieving mechanism.

12. The delivery apparatus of claim 10, wherein the releasable holding of the first end of the holding and retrieving mechanism is achieved with an elastic hook which holds one end of the holding and retrieving mechanism in an aperture near the distal end of the elongated tubular member.

13. The delivery apparatus of claim 10, wherein the releasable holding of the first end of the holding and retrieving mechanism is achieved with pliers configured to releasably hold the first end of the holding and retrieving mechanism.

14. The delivery apparatus of claim 10, wherein the releasable holding of the first end of the holding and retrieving mechanism is achieved using a coaxial element movable relative to the elongated member; which comprises a sharp window, wherein the inner edge of said sharp window is configured to cut the holding and retrieving mechanism, and wherein the holding and retrieving mechanism passes through the sharp window.

15. The delivery apparatus of claim 10, wherein said second expandable portion comprises a balloon and said first portion comprises a channel in fluid communication with the balloon for injecting a fluid into the balloon so as to expand the balloon.

16. The delivery apparatus of claim 10, wherein said second expandable portion comprises a flexible member comprising a proximal end and a distal end; and said first portion comprises an actuator engaged with the distal end of the flexible member; wherein in response to a proximal movement of the actuator relative to the proximal end of the flexible member, the flexible member expands to the expanded profile.

17. The delivery apparatus of claim 16, wherein the proximal end of the flexible member is secured to the distal end of the elongated tubular member.

18. The delivery apparatus of claim 10, wherein
the holding and retrieving mechanism comprises a longitudinal axis and the ratio between the length along the longitudinal axis and the greater length in the transverse plane is greater than 3.

19. The delivery apparatus of claim 18, wherein
the releasable holding of the first end of the holding and retrieving mechanism is achieved with a first aperture and a second aperture through the elongated tubular member from the lumen to an outer wall, said first and second apertures being disposed near the distal end of the elongated tubular member and said first aperture being disposed proximally of said second aperture; and a trigger wire disposed within the lumen of the elongated tubular member; the trigger wire exits said lumen of said elongated tubular member through the first aperture and re-enters said lumen of said elongated tubular member through the second aperture such that said trigger wire forms a bend, said bend of said trigger wire engaging said first end of the holding and retrieving mechanism; said trigger wire being configured to be withdrawn in the proximal direction through said lumen of said elongated tubular member such that said trigger wire disengages said first end of the holding and retrieving mechanism.

20. A delivery apparatus for delivering a radially self-expanding medical device having a proximal portion and a distal portion, said delivery apparatus comprising:
  i. a radially self-expanding medical device having a proximal end and a distal end;
  ii. an elongated tubular member having a proximal end, a distal end, and a lumen extending along a longitudinal axis from the proximal end to the distal end;
  iii. a sheath, said sheath being coaxially disposed around the elongated tubular member; wherein the elongated tubular member is movable relative to the sheath; and wherein the sheath is configured for receiving the radially self-expanding medical device in a radially compressed state; and
  iv. a holding and retrieving mechanism having a first end and a second end; the holding and retrieving mechanism being configured to constrain radially the proximal portion of the radially self-expanding medical device such that in response to a proximal movement of the elongated tubular member relative to the sheath, the holding and retrieving mechanism constrains radially the proximal portion of the radially self-expanding medical device and the radially self-expanding medical device is collapsed within the sheath;
wherein the elongated tubular member is capable of releasably holding the first end of the holding and retrieving mechanism near the distal end of the elongated tubular member and releasing the first end by an actuation at the proximal end of the elongated tubular member; and wherein the holding and retrieving mechanism is connected only to the proximal end of the radially self-expanding medical device;
wherein the elongated tubular member non-detachably holds the second end of the holding and retrieving mechanism near the distal end of the elongated tubular member with a hook and the second end of the holding and retrieving mechanism comprises a loop configured to be hooked to the hook of the elongated tubular member;
wherein the holding and retrieving mechanism comprises a longitudinal axis and the ratio between the length along the longitudinal axis and the greater length in the transverse plane is greater than 3;
wherein the releasable holding of the first end of the holding and retrieving mechanism is achieved with a first aperture and a second aperture through the elongated tubular member from the lumen to an outer wall, said first and second apertures being disposed near the distal end of the elongated tubular member and said first aperture being disposed proximally of said second aperture; and a trigger wire disposed within the lumen of the elongated tubular member; the trigger wire exits said lumen of said elongated tubular member through the first aperture and re-enters said lumen of said elongated tubular member through the second aperture such that said trigger wire forms a bend, said bend of said trigger wire engaging said first end of the holding and retrieving mechanism; said trigger wire being configured to be withdrawn in the proximal direction through said lumen of said elongated tubular member such that said trigger wire disengages said first end of the holding and retrieving mechanism.

* * * * *